(12) United States Patent
Fornof et al.

(10) Patent No.: US 9,730,864 B2
(45) Date of Patent: Aug. 15, 2017

(54) ADDITION-FRAGMENTATION OLIGOMERS HAVING HIGH REFRACTIVE INDEX GROUPS

(71) Applicant: 3M INNOVATIVE PROPERTIES COMPANY, St. Paul, MN (US)

(72) Inventors: Ann R. Fornof, Austin, TX (US); William H. Moser, Edina, MN (US); Guy D. Joly, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/112,220

(22) PCT Filed: Feb. 10, 2015

(86) PCT No.: PCT/US2015/015102
§ 371 (c)(1),
(2) Date: Jul. 18, 2016

(87) PCT Pub. No.: WO2015/126657
PCT Pub. Date: Aug. 27, 2015

(65) Prior Publication Data
US 2016/0346170 A1 Dec. 1, 2016

Related U.S. Application Data

(60) Provisional application No. 61/940,937, filed on Feb. 18, 2014.

(51) Int. Cl.
| | | |
|---|---|---|
| *A61K 6/083* | (2006.01) | |
| *A61F 2/00* | (2006.01) | |
| *C08G 61/02* | (2006.01) | |
| *C08G 61/04* | (2006.01) | |
| *A61K 6/00* | (2006.01) | |
| *C09J 4/06* | (2006.01) | |
| *B32B 37/10* | (2006.01) | |
| *B32B 37/12* | (2006.01) | |
| *C09D 4/00* | (2006.01) | |
| *C09J 4/00* | (2006.01) | |

(52) U.S. Cl.
CPC .......... *A61K 6/0835* (2013.01); *A61K 6/0005* (2013.01); *B32B 37/10* (2013.01); *B32B 37/12* (2013.01); *C09D 4/00* (2013.01); *C09J 4/00* (2013.01); *C09J 4/06* (2013.01); *B32B 2255/26* (2013.01); *B32B 2305/72* (2013.01)

(58) Field of Classification Search
None
See application file for complete search history.

(56) References Cited

U.S. PATENT DOCUMENTS

| | | |
|---|---|---|
| 2,801,185 A | 7/1957 | Iler |
| 3,496,250 A | 2/1970 | Czerwinski |
| 4,503,169 A | 3/1985 | Randklev |
| 4,522,958 A | 6/1985 | Das |
| 4,547,323 A | 10/1985 | Carlson |
| 4,886,861 A | 12/1989 | Janowicz |
| 5,130,347 A | 7/1992 | Mitra |
| 5,154,762 A | 10/1992 | Mitra |
| 5,324,879 A | 6/1994 | Hawthorne |
| 5,501,727 A | 3/1996 | Wang |
| 5,506,279 A | 4/1996 | Babu |
| 5,545,676 A | 8/1996 | Palazzotto |
| 5,925,715 A | 7/1999 | Mitra |
| 5,962,550 A | 10/1999 | Akahane |
| 6,126,922 A | 10/2000 | Rozzi |
| 6,387,981 B1 | 5/2002 | Zhang |
| 6,572,693 B1 | 6/2003 | Wu |
| 6,586,483 B2 | 7/2003 | Kolb |
| 6,670,436 B2 | 12/2003 | Burgath |
| 6,730,156 B1 | 5/2004 | Windisch |
| 6,794,520 B1 | 9/2004 | Moszner |
| 6,893,731 B2 | 5/2005 | Kausch |
| 7,090,721 B2 | 8/2006 | Craig |
| 7,090,722 B2 | 8/2006 | Budd |
| 7,156,911 B2 | 1/2007 | Kangas |
| 7,241,437 B2 | 7/2007 | Davidson |
| 7,649,029 B2 | 1/2010 | Kolb |
| 7,674,850 B2 | 3/2010 | Karim |

(Continued)

FOREIGN PATENT DOCUMENTS

| | | |
|---|---|---|
| WO | WO 01-30305 | 5/2001 |
| WO | WO 01-30307 | 5/2001 |

(Continued)

OTHER PUBLICATIONS

Mitra et al, WO 2008-082881 Machine Translation, Jul. 10, 2008.*
Cara, "Influence of Bis-GMA Derivative Monomer-Based Particulate Composite Resins on the Cuspal Deformation and Microleakage of Restored Teeth", Particulate Science and Technology, 2010, vol. 28, pp. 191-206.
Enikolopyan, "Catalyzed Chain Transfer to Monomer in Free Radical Polymerization", Journal of Polymer Science, 1981, vol. 19, pp. 879-889.
Kloxin, "Stress Relaxation via Addition-Fragmentation Chain Transfer in a Thiol-ene Photopolymerization", Macromolecules, 2009, vol. 42, pp. 2551-2556.
Temel, "Photopolymerization and photophysical properties of amine linked benzophenone photoinitiator for free radical polymerization", Journal of Photochemistry and Photobiology A: Chemistry, 2011, vol. 219, pp. 26-31.

(Continued)

*Primary Examiner* — Jessica E Whiteley
(74) *Attorney, Agent, or Firm* — Kent S. Kokko

(57) ABSTRACT

Addition-fragmentation oligomers of the general formula $Z-B_y-A-(B-A)_x-B-A-B_y-Z$, where the A monomers units are derived from a diester or diacid, the B monomer units are derived from a difunctional monomer having functional groups co-reactive with the acid or ester groups of the A monomer, x+y is zero to 60, Z comprises an ethylenically unsaturated, polymerizable group, A monomers comprise a 1-methylene-3,3-dimethylpropyl group, and at least one B monomer unit comprises a high refractive index group.

18 Claims, No Drawings

(56) References Cited

U.S. PATENT DOCUMENTS

| | | |
|---|---|---|
| 7,838,110 B2 | 11/2010 | Zhu |
| 7,888,400 B2 | 2/2011 | Abuelyaman |
| 7,943,680 B2 | 5/2011 | Bowman |
| 2005/0017966 A1 | 1/2005 | Engl |
| 2008/0076848 A1 | 3/2008 | Jin |
| 2009/0011388 A1 | 1/2009 | Craig |
| 2010/0021869 A1 | 1/2010 | Abuelyaman |
| 2011/0041736 A1 | 2/2011 | Gartner |
| 2012/0208965 A1 | 8/2012 | Joly |
| 2013/0109777 A1 | 5/2013 | Eckert |
| 2015/0328086 A1* | 11/2015 | Fornof ............ C08F 2/38 433/217.1 |

FOREIGN PATENT DOCUMENTS

| | | | |
|---|---|---|---|
| WO | WO 03-063804 | | 8/2003 |
| WO | 2008082881 | * | 7/2008 |
| WO | WO 2008-082881 | | 7/2008 |
| WO | WO 2009-091551 | | 7/2009 |
| WO | WO 2011-126647 | | 10/2011 |
| WO | WO 2012-112321 | | 8/2012 |
| WO | WO 2012-112350 | | 8/2012 |
| WO | WO 2013-028397 | | 2/2013 |
| WO | WO 2013-028401 | | 2/2013 |
| WO | WO 2014-074373 | | 5/2014 |
| WO | WO 2014-074427 | | 5/2014 |
| WO | WO 2014-151363 | | 9/2014 |

OTHER PUBLICATIONS

Watts, "Determination of polymerization shrinkage kinetics in visible-light-cured materials: methods development", Dental Materials, 1991, vol. 7, pp. 281-287.

International Search Report for PCT International Application No. PCT/US2015/015102, mailed on Apr. 17, 2015, 5 pages.

* cited by examiner

ADDITION-FRAGMENTATION OLIGOMERS HAVING HIGH REFRACTIVE INDEX GROUPS

CROSS REFERENCE TO RELATED APPLICATIONS

This application is a national stage filing under 35 U.S.C. 371 of PCT/US2015/015102, filed Feb. 10, 2015, which claims the benefit of U.S. Application No. 61/940,937, filed Feb. 18, 2014, the disclosure of which is incorporated by reference in its/their entirety herein.

BACKGROUND

The present disclosure provides novel addition-fragmentation oligomers for use in low-stress polymerizable compositions. Free-radical polymerization is typically accompanied by a reduction in volume as monomers are converted to polymer. The volumetric shrinkage produces stress in the cured composition, leading to microcracks and deformation. Stress transferred to an interface between the cured composition and a substrate can cause failure in adhesion and can affect the durability of the cured composition.

The crosslinking oligomers of this disclosure provide stress relief by including labile crosslinks that can cleave and reform during the polymerization process. Crosslink cleavage may provide a mechanism to allow for network reorganization, relieve polymerization stress, and prevent the development of high stress regions. The instant crosslinking oligomer may further provide stress relief by delaying the gel point, the point at which the polymerizable composition transitions from a viscous material to a viscoelastic solid. The longer the polymerizable mixture remains viscous, the more time available during which material flow can act to alleviate stress during the polymerization process.

The addition-fragmentation oligomers provide novel stress-reducing oligomers that have application in dental compositions, thin films, hardcoats, composites, adhesives, and other uses subject to stress reduction.

SUMMARY

The present disclosure provides addition-fragmentation oligomers having the following functional groups: 1) labile addition-fragmentation groups that can cleave and reform to relieve strain, 2) at least one high refractive index group, and 3) ethylenically unsaturated, polymerizable groups.

The addition-fragmentation crosslinking oligomers provide novel stress-reducing crosslinking oligomers that have application in dental restoratives, thin films, hardcoats, composites, adhesives, and other uses subject to stress reduction. In addition, the addition-fragmentation process of crosslinking results in a chain-transfer event that provides novel polymers that may be further functionalized.

The present disclosure provides addition-fragments oligomers of the general formula:
$Z$—$B_y$-$A$-$(B$-$A)X$—$B$-$A$-$B_y$—$Z$, where the A monomers units are derived from a diester or diacid of a 1-methylene-3,3-dimethylpropyl group, the B monomer units are derived from a difunctional monomer having functional groups co-reactive with the acid or ester groups of the A monomer, x and y is 0 or 1, Z comprises an ethylenically unsaturated, polymerizable group, and at least one of B monomer units comprise a high refractive index group, which may be in-chain or pendent from the B unit chain. Preferably at least 50% of the B units contain a high refractive index group, more preferably at least 75% of the B units contain a high refractive index group When added to a mixture of polymerizable monomers, the high refractive index groups of the oligomer may increase the refractive index of the resulting polymer. In addition, it has been observed that incorporation of high refractive index groups increases the depth of cure during a UV initiated polymerization process, by reducing light-scattering due to mismatched refractive indices.

More particularly, the present disclosure provides addition-fragmentation oligomers of Formula I:

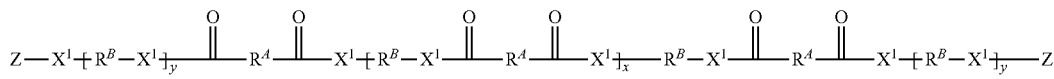

wherein
$R^A$ is

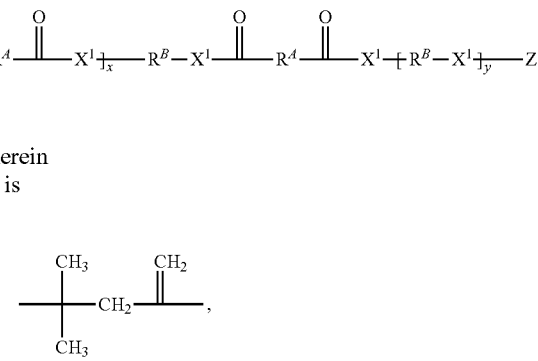

$R^B$ a (hetero)hydrocarbyl group, wherein at least one $R^B$ contains a high refractive index group, preferably a majority of the $R^B$ units are so substituted,
$X^1$ is —O— or $NR^5$—, where $R^5$ is H or $C_1$-$C_4$ alkyl;
$Z$ comprises an ethylenically unsaturated polymerizable group;
$y$ is 0 or 1;
$x$ is 0 or 1.

When x and y are both zero, the oligomer will have three monomer units. In some embodiments y is 1 or x is at least 1. In some preferred embodiments x and y are 0. In some embodiments x+y is zero to 60, and preferably 0 to 20. It will be appreciated that Formula I may be a mixture of oligomers, so the average value of x and y may be non-integral. In some preferred embodiments, x+y is 1-10.

The addition-fragmentation oligomer of Formula I may be added to polymerizable monomer mixtures to reduce the polymerization-induced stresses. As the addition-fragmentation oligomer has two ethylenically unsaturated "Z" groups, the oligomers further function as addition-fragmentation crosslinking oligomers, where the crosslinks are labile. This disclosure further provides a method of preparing the addition-fragmentation oligomers of Formula I, as further disclosed herein.

This disclosure further provides a polymerizable composition comprising the addition-fragmentation oligomer and one or more free-radically polymerizable monomers, the addition-fragmentation oligomer providing a reduction in shrinkage and stress of the resultant polymers. The addition-fragmentation oligomers act as chain-transfer oligomers via an addition-fragmentation process whereby the crosslinks are labile during polymerization and continuously cleave and reform, providing a reduction in polymerization-based stress.

In some embodiments, the polymerizable composition may be used in coatings, particularly hardcoats.

As used herein:

"(meth)acryloyl" includes both acryloyl and methacryloyl groups; i.e. is inclusive of both esters and amides;

"curable" or "polymerizable" means that a composition can be transformed into a solid, substantially non-flowing material by means of free-radical polymerization, chemical cross linking, radiation crosslinking, or the like;

"alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e monvalent alkyl or polyvalent alkylene;

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent, i.e. monovalent heteroalkyl or polyvalent heteroalkylene;

"aryl" is an aromatic group containing 5-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene;

"(hetero)hydrocarbyl" is inclusive of hydrocarbyl alkyl and aryl groups, and heterohydrocarbyl heteroalkyl and heteroaryl groups, the latter comprising one or more catenary (in-chain) oxygen or nitrogen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

DETAILED DESCRIPTION

The present disclosure provides addition-fragmentation oligomers of the Formula I, supra.

The present disclosure provides addition-fragmentation oligomers having the following functional groups: 1) labile addition-fragmentation groups ($R^4$) that can cleave and reform to relieve strain, 2) free-radically polymerizable groups (Z) which may crosslink a polymer and units containing high refractive index groups ($R^B$). The crosslinked polymer may be crosslinked in situ by polymerizing the addition-fragmentation oligomer in the presence of free-radically polymerizable monomers, or an extant polymer having polymerizable groups may be combined with the addition-fragmentation oligomer and crosslinked.

The addition-fragmentation oligomers may be added to polymerizable monomer mixtures to reduce the polymerization-induced stresses. In some embodiments, the oligomers further function as addition-fragmentation crosslinking oligomers, where the crosslinks are labile. This disclosure further provides a method of preparing the addition-fragmentation oligomers of Formula I, as further disclosed herein.

This disclosure further provides a curable composition comprising the addition-fragmentation oligomers and one or more free-radically polymerizable monomers, the addition-fragmentation oligomer providing a reduction in stress of the resultant polymers. The addition-fragmentation oligomers act as chain-transfer oligomers via an addition-fragmentation process whereby the crosslinks are labile during polymerization and continuously cleave and reform, providing a reduction in polymerization-based stress.

In many embodiments, the effect of the addition-fragmentation functionality (stress relief) can be independent of the crosslink density by controlling the molecular weight of the oligomer. In some embodiments, the weight of addition fragmentation oligomers needed is less than a structurally equivalent (i.e. linking groups and end groups) non-oligomeric addition-fragmentation oligomer for the same level of stress relaxation. Further, the instant addition-fragmentation oligomers have higher viscosity than comparable non-oligomeric addition-fragmentation agent, which may be used to modify viscosity, which can be desirable for certain coating techniques.

It is believed that the addition-fragmentation oligomer follows an addition fragmentation pathway as shown in the following Scheme 1. In this scheme the addition-fragmentation oligomeric crosslinking oligomer of Formula I is shown in simplified form with "Oligo" representing the oligomeric chain. In the step 1, a free radical species P. adds to the crosslinking oligomer. The crosslinking oligomer then fragments as shown in step 2 to form the relatively stable α-carbonyl tertiary radical and the α,β-unsaturated ester bearing the residue of the free radical species P. This α,β-unsaturated ester can undergo radical addition as shown in step 5. The radical addition may be initiated by an initiator or a polymer radical.

Concurrently the α-carbonyl tertiary radical can initiate polymerization of monomer as shown in step 3. For purposes of illustration, a methacrylate monomer is illustrated. On monomer addition, a methacrylate terminated radical intermediate is produced. In the presence of the crosslinking oligomer of Formula 1 (as shown in step 4) both addition, and fragmentation, yielding a tertiary radical, occurs.

The bonds between the ethylenically unsaturated Z groups will form labile bonds. Fragmentation of the addition-fragmentation crosslinking oligomer provides a mechanism for crosslink cleavage. The cleavage of labile addition-fragmentation groups may allow the polymeric network to relax or reorganize, especially in high stress regions, providing a potential mechanism for stress relief where the B compound comprises a high refractive index group, or contains a functional group that may be further reacted to provide the high refractive index group; and a compound of the formula:

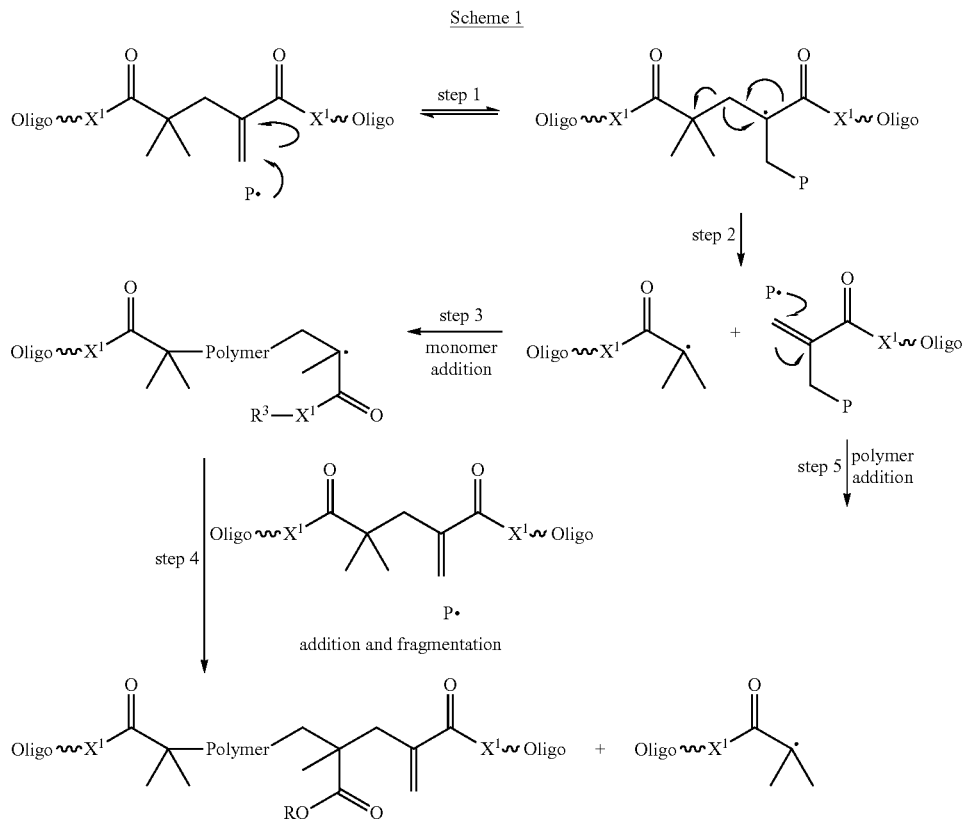

Scheme 1

Stress relief could also be a result of attenuated reaction rates (slower cure rates) in the presence of addition-fragmentation materials. The addition of a radical to the addition-fragmentation crosslinking oligomer generates a potentially long-lived, tertiary radical (the product of step 1, Scheme 1). This long-lived radical intermediate can revert back to starting materials, add to monomer, or fragment. If fragmentation, retro-addition and monomer addition are slow relative to addition, the intermediate tertiary radical will be relatively long-lived. This long-lived radical intermediate will then act as a radical reservoir, slowing down the overall polymerization process. Attenuated cure rates could serve to delay the transition of a material from a viscous material to a viscoelastic solid, delaying the gel point. Post-gel shrinkage is a major component in stress development; therefore, delaying the gel point even slightly may lead to stress relief by allowing additional time for material to flow during the curing process.

The addition-fragmentation oligomers of Formula I may be prepared by reaction between compounds of the formula:
a) $R^1$—O—CO—$R^A$—CO—O—$R^1$, "A compound" wherein $R^A$ is a 1-methylene-3,3-dimethyl propyl group and $R^1$ is H, an alkyl an aryl or alkyl and is optionally substituted with a reactive nucleophilic or electrocphilic functional group, i.e., $R^1$ is $R^{FG}$;
and a compound of the formula:
b) $X^2$—$R^B$—$X^2$, "B compound", wherein $R^B$ is a (hetero) hydrocarbyl group and $X^2$ comprises a functional group reactive with the functional groups of the A compound, c) $(Z)_d$—$X^3$, "C compound" where Z comprises an ethylenically unsaturated group, and $X^3$ is a reactive functional group, reactive with the acid or ester groups, or the $X^2$ groups, d is 1 or 2; and
d) optionally further functionalizing the B units of the oligomer resulting from the reaction of the A and B compounds with a high refractive index group. In some embodiments, reaction of the A and B compounds yields a functional group that may be further functionalized. In some embodiments the B compound may comprise a high refractive index group.

The A compounds comprise a 1-methylene-3,3-dimethyl propyl group that may be prepared from methacrylate dimers by substitution, displacement or condensation reactions. The starting methacrylate dimers may be prepared by free radical addition of a (meth)acryloyl monomer in the presence of a free radical initiator and a cobalt (II) complex catalyst using the process of U.S. Pat. No. 4,547,323 (Carlson), incorporated herein by reference. Alternatively, the (meth)acryloyl may be prepared using a cobalt chelate complex using the processes of U.S. Pat. No. 4,886,861 (Janowicz) or U.S. Pat. No. 5,324,879 (Hawthorne), incorporated herein by reference. In either process, the reaction mixture can contain a complex mixture of dimers, trimers, higher oligomers and polymers and the desired dimer can be separated from the mixture by distillation and/or recrystallization. Distillation further separates any cobalt species from the desired dimer, which is detrimental to the polymerizable composition described herein, as the $Co^{II}$ and/or $Co^{III}$ species enhances the rate of dimerization relative to addition polymerization. It is preferred that the addition-fragmentation oligomers of Formula I contain less than 0.01 wt. % cobalt compounds.

In some embodiments the $R^1$ group of the A compound is $R^{FG}$, where $R^{FG}$ contains a reactive functional group, reactive with the $X^2$ groups of the B compounds and/or the $X^3$ groups of the C compounds. In such instances, further functionalization of the B units is optional, but not required. More particularly, $R^{FG}$ is an aryl or an alkyl further substituted with a nucleophilic or electrophilic functional group, such as a alkylenes or arylenes having a hydroxyl, amino, isocyanate, and other nucleophilic or electrophilic reactive functional groups described with respect to the $X^2$ and $X^3$ groups.

The reaction may be a single step where each of compounds A and B and optionally steps c) or d) are combined and allowed to react to produce an intermediate oligomer, which may be further functionalized to provide the Z groups and the high refractive index groups. Alternatively the steps may be sequential where compounds a) and b) are first reacted, followed by end-capping the oligomer with compound C and functionalization with a high refractive index group, in either order. The condensation or addition of the reactants may be neat or one may use a suitable solvent. Alternatively, the B compounds contain the requisite high refractive index groups, in which A and B are oligomerized to produce the intermediate oligomer, then end-capped to provide the Z groups.

For a given A compound having a reactive nucleophilic or electrophilic functional group, the B compound is chosen such that the functional groups $X^2$ thereof are co-reactive with the those of the A compound. Depending on the relative amounts of the A and B compounds, the intermediate will be terminated in either —$CO_2R^1$ groups (having the associated functional groups of the A compounds), or $X^2$ groups of the B compounds. Simply, the intermediate oligomer resulting from the reaction between the A and B compounds may have the structure The addition fragmentation of claim 7 where reaction between the A compounds and B compounds yields an intermediate oligomer of the formula:
A and B compounds may have the structure The functional groups of the end-capping compounds, to provide the Z groups are selected to be reactive with the terminal functional groups of the intermediate. With functionalization of the end groups, the addition fragmentation oligomers have the simplified structures Z-A-(B-A)-B-A-Z or Z—B-(A-B)-A-B—Z. If the B units do not contain a high refractive index group, all or a portion of the B units are further functionalized. Preferably at least 50% of the B units are so functionalized, more preferably at least 75%.

Useful reactive (and co-reactive) functional groups include hydroxyl, secondary amino, oxazolinyl, oxazolonyl, acetylacetonate, carboxyl, ester, isocyanato, epoxy, aziridinyl, acyl halide, and cyclic anhydride groups. Most generally, the reaction is between a nucleophilic and electrophilic functional groups. Where the reactive functional group of the A compound comprises a carboxylic acid group ($R^1$=H), the co-reactive functional group $X^2$ of the B compound preferably comprises a hydroxyl, amino, epoxy, isocyanate, aziridinyl or oxazolinyl group. Where the reactive functional group of the A compound is an ester functional group, the co-reactive functional group preferably comprises an amino or hydroxyl group. Conversely, when the functional group of the A compound ($R^{FG}$) is an electrophilic functional group such as anepoxy, isocyanate or aziridine group, the coreactive functional group is a nucleophilic functional group such as a hydroxy, amino, thiol group.

In some embodiments, the B compound comprises a (hetero)hydrocarbyl compound having two nucleophilic or electrophilic functional groups, co-reactive with the functional groups of the A compound, and at least one additional functional group that may be further functionalized to provide the high refractive index group. Useful B compounds including diols, diisocyanates, diaziridines, di-epoxies, including difunctional esters, such as hydroxyalkyl esters and amides, isocyanatoalkyl esters and amides, and glycidyl esters.

In a preferred embodiment, the A compound is a diacid, where $R^1$ is H and the B compound is a diepoxy or diaziridine. Reaction thereof occurs through ring-opening of the epoxy, yielding a —$CH_2$—CH(OH)$CH_2$— linkage, the

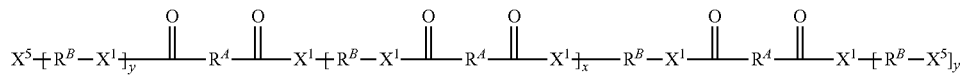

wherein
$R^A$ is

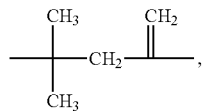

$R^B$ a (hetero)hydrocarbyl group, wherein at least one $R^B$ contains a high refractive index group,
$X^1$ is —O— or $NR^5$—, where $R^5$ is H or $C_1$-$C_4$ alkyl;
Z comprises an ethylenically unsaturated polymerizable group;
$X^5$ is a terminal functional group selected from —$OR^1$ of the A compounds or $X^2$ of the B compounds;
y is 0 or 1;
x is 0 or 1.

hydroxyl thereof then further functionalized to provide the requisite high refractive index groups.

In some preferred embodiments, the reaction of a nucleophilic functional A compound with an epoxy-functional B compound will yield a hydroxy-functional linking group. Similarly, the reaction of a nucleophilic functional A compound with an aziridine-functional B compound will yield an amine-functional linking group. For example, in a reaction with a diepoxy compound the epoxy group will yield a 2-hydroxypropyl group, corresponding to $R^B$ of Formula I. This may be further functionalized with compounds having a high refractive index group as shown in the Examples.

In some embodiments, the intermediate oligomer from the A and B compounds has terminal epoxy groups, such as when a nucleophilic functional A compound is reacted with an excess of diepoxy B compound. This oligomeric intermediate may be represented as Epoxy-B-(A-B)-A-B-Epoxy. This intermediate may be functionalized with a C compound of the formula $(Z)_d$—$X^3$, where the $X^3$ group is a nucleophilic group reactive with the terminal epoxy groups. Reaction between the oligomeric intermediate and the nucleophilic C compound ring-open the epoxy group, provide the requisite Z group, and further provide a hydroxy group, that may be further functionalized to provide the high refractive index group.

Similarly, an excess of diaziridine B compound may be so reacted to provide an intermediate oligomer having terminal aziridine groups that may be reacted with a C compound having nucleophilic functional groups, which ring-open the aziridine to provide amine groups that may be further functionalized with the high refractive index group.

In some embodiments, the A compound comprises a reactive functional group, $R^{RF}$, comprising an epoxy group or an aziridine group, such as glycidyl esters or alkylaziridine esters of the A compounds. The B compound may be selected as having nucleophilic functional groups. Reaction between these results in a hydroxyalkyl group (from a glycidyl ester) or an aminoalkyl group (from the alkylaziridine). The amine or hydroxyl then may be further functionalized with the high refractive index group.

In other embodiments, an excess of A compounds having nucleophilic functional groups are reacted with B compounds having electrophilic functional groups to provide an oligomeric intermediate having terminal nucleophilic functional groups. This intermediate is reacted with a C compound of the formula $(Z)_d$—$X^3$, where $X^3$ is an epoxy or aziridine group. Ring-opening of the X3 group yields a hydroxy or amine group that may be further functionalized to provide the high refractive index group.

In another embodiment, A compounds having nucleophilic functional groups are reacted with an excess of B compounds having electrophilic functional groups to provide an oligomeric intermediate having terminal electrophilic groups. This may be functionalized with C compounds having nucleophilic $X^3$ groups. In some embodiments these terminal electrophilic functional groups are aziridine or epoxy functional groups.

In other embodiments, an excess of A compounds having electrophilic functional groups are reacted with B compounds having nucleophilic functional groups to provide an oligomeric intermediate having terminal electrophilic functional groups. This may be functionalized with C compounds having nucleophilic $X^3$ groups. In some embodiments these terminal electrophilic functional groups are aziridine or epoxy functional groups.

In other embodiments, A compounds having electrophilic functional groups are reacted with an excess of B compounds having nucleophilic functional groups to provide an oligomeric intermediate having terminal nucleophilic functional groups. This may be reacted with C compounds having electrophilic functional groups. In some embodiments, the electrophilic functional groups of the C compound may be epoxy or aziridine functional groups.

Similarly, A compounds having nucleophilic functional groups are reacted with an excess of B compounds having electrophilic functional groups to provide an oligomeric intermediate having terminal nucleophilic functional groups. Again, this intermediate is reacted with a C compound of the formula $(Z)_d$—$X^3$, where $X^3$ is an epoxy or aziridine group. Ring-opening of the $X^3$ group yields a hydroxy or amine group that may be further functionalized to provide the high refractive index group.

In other embodiments, the B compound of the formula $X^2$—$R^B$—$X^2$ is selected such that $R^B$ contains a high refractive index group; i.e. $R^B$ is $R^{B-RI}$, and nucleophilic or electrophilic $X^2$ groups. This may be oligomerized with A compounds having co-reactive functional groups to produce an intermediate oligomer, which may then be functionalized with the requisite Z groups. When RB is $R^{B-RI}$, a subsequent functionalization step to provide the oligomer is optional, but additional high refractive index groups may be added if the oligomer is terminated in epoxy or aziridine groups and reacted with C compounds having nucleophilic groups, or the intermediate oligomer is terminated in nucleophilic groups, and the C compound has an aziridine or epoxy $X^3$ group.

Useful $R^{B-RI}$ groups of the C compounds may include benzyl, 2-, 3-, and 4-biphenyl, 1-, 2, 3-, 4-, and 9-fluorenyl, 4-(1-methyl-1-phenethyl)phenoxyethyl; phenylthio; 1-, 2-, 3- and 4-napthyl, 1- and 2-naphthylthio; 2,4,6-tribromophenoxy; 2,4-dibromophenoxy; 2-bromophenoxy; 1-, and 2-naphthyloxy; 3-phenoxy-; 2-, 3- and 4-phenylphenoxy; 2,4-dibromo-6-sec-butylphenyl; 2,4-dibromo-6-isopropylphenyl; 2,4-dibromophenyl; pentabromobenzyl and pentabromophenyl With reference to Formula I, the requisite ethylenically unsaturated "Z" group may be incorporated into the A-B oligomer intermediate by means including addition, condensation, substitution and displacement reaction. The ethylenically unsaturated moiety, Z, may include, but is not limited to the following structures, including (meth)acryloyl, vinyl, styrenic and ethynyl, that are more fully described in reference to the preparation of the compounds below.

In general, the terminal ethylenically unsaturated functional groups of the oligomer is provided with the Z-group of Formula I by reaction with a compound of the general formula $(Z)_d$—$X^3$ ("C compound"), where Z comprises an ethylenically unsaturated group, and $X^3$ is reactive functional group, reactive with the acid or ester groups of the A compound, or the $X^2$ groups of the B compound and d is 1 or 2.

More particularly, the "C" compound may be of the formula: $Y^1$—$R^3$—O—CO—$CR^2$=$CH_2$, where $Y^1$ is an electrophilic functional group reactive with carboxylic acid groups, $R^3$ is a (hetero)hydrocarbyl group, preferably alkylene, $R^2$ is H or $CH_3$, or of the formula $Y^2$—$R^3$—O—CO—$CR^2$=$CH_2$, where $Y^2$ is an nucleophilic functional group reactive with carboxylic ester groups or electrophilic functional groups, $R^3$ is (hetero)hydrocarbyl group, preferably alkylene, and $R^2$ is H or $CH_3$.

Generally, the oligomeric intermediate is reacted with an unsaturated C compound of the formula:

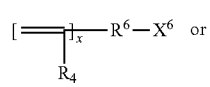

IIIa

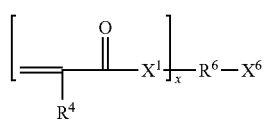

IIIb wherein
$X^6$ is a functional group that is co-reactive with functional group of the A or B compound,
$R^4$ is hydrogen, a $C_1$ to $C_4$ alkyl group, $R^6$ is a single bond or a divalent (hetero)hydrocarbyl linking group that joins the ethylenically unsaturated group to reactive functional group $X^6$, and x is 1 or 2.

More specifically, $R^6$ is a single bond or a divalent linking group that joins an ethylenically unsaturated group to co-reactive functional group $X^6$ and preferably contains up to 34, preferably up to 18, more preferably up to 10, carbon atoms and, optionally, oxygen and nitrogen atoms, optional catenary (in-chain) ester, amide, urea, urethane and carbonate groups. When $R^6$ may further include linking groups selected from —O—, —S—, —NR$^4$—, —SO$_2$—, —PO$_2$—, —CO—, —OCO—, —NR$^5$—CO—, NR$^5$—CO—O—, NR$^5$—CO—NR$^4$—, —R$^7$— and combinations thereof, such as —CO—O—R$^7$—, —CO—NR$^5$—R$^7$—, and —R$^7$—CO—O—R$^7$—, wherein each $R^5$ is hydrogen, a $C_1$ to $C_4$ alkyl group, or aryl group, each $R^7$ is an alkylene group having 1 to 6 carbon atoms, a 5- or 6-membered cycloalkylene group having 5 to 10 carbon atoms, or a divalent aromatic group having 6 to 16 carbon atoms; and $X^6$ is a reactive functional group capable of reacting with a co-reactive functional group for the incorporation of a free-radically polymerizable functional "Z" group. In some embodiments, $R^6$ is a $C_2$-$C_8$ alkylene.

It will be understood that reaction between the terminal functional groups of the oligomeric intermediate and the $X^6$ group of Formulas III will form the Z—$X^1$— moiety of Formula I, with the proviso that —$X^1$—Z does not contain peroxidic linkages, i.e. O—O, N—O, S—O, N—N, N—S bonds.

In reference to Formula I, particularly useful Z—$X^1$— groups include H$_2$C=C(CH$_3$)C(O)—O—CH$_2$—CH(OH)—CH$_2$—O—, H$_2$C=C(CH$_3$)C(O)—O—CH$_2$—CH(O—(O)C(CH$_3$)=CH$_2$)—CH$_2$—O—, H$_2$C=C(CH$_3$)C(O)—O—CH(CH$_2$OPh)-CH$_2$—O—, H$_2$C=C(CH$_3$)C(O)—O—CH$_2$CH$_2$—N(H)—C(O)—O—CH(CH$_2$OPh)-CH$_2$—O—, H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(OH)—CH$_2$—O—, H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, CH$_3$—(CH$_2$)$_7$—CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(—O—(O)C(H)=CH$_2$)—CH$_2$—O— and H$_2$C=C(H)C(O)—O—CH$_2$—CH(OH)—CH$_2$—O—. H$_2$C=C(H)C(O)—O—(CH$_2$)$_4$—O—CH$_2$—CH(—O—(O)C(H)=CH$_2$)—CH$_2$—O—, and CH$_3$—(CH$_2$)$_7$—CH(O—(O)C—N(H)—CH$_2$CH$_2$—O—(O)C(CH$_3$)C=CH$_2$)—CH$_2$—O—.

Similar to incorporation of the Z group, a portion of the RB units may be reacted with a compound of the formula:
$(R^{RI})_d$—$X^5$,    VI where $R^{RI}$ comprises high refractive index group, and $X^5$ is a reactive functional group, reactive with the reactive functional groups on the B monomer units of the oligomer, and subscript d is at least 1. As described for the Z group, the requisite high refractive index group may be incorporated into the intermediate by means including addition, condensation, substitution and displacement reaction. Once functionalized, the pendent high refractive index groups may be represented as $(R^{RI})_d$—$X^{5*}$, where $X^{5*}$ represents the inking groups resulting from reaction between the electrophilic and nucleophilic functional groups.

More particularly, the compound of Formula VI may be of the formula:

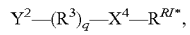    VIa where $Y^1$ is an electrophilic functional group reactive with nucleophilic $X^2$ groups or nucleophilic groups on the B units, $R^3$ is a (hetero)hydrocarbyl group, preferably alkylene, q is 0 or 1, $X^4$ is selected from a covalent bond or a divalent linking group including —O—, —O—CO—, —O—CO—NH—, —S—, —NH—, —NH—CO—, —NH—CO—NH, —NH—CO—O—, —O—CO—NH and $R^{RI*}$ is a high refractive index group;
or is of the formula

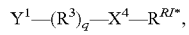    VIb where $Y^2$ is an nucleophilic functional group reactive with electrophilic $X^2$ groups or electrophilic groups on the B units, $R^3$ is (hetero)hydrocarbyl group, preferably alkylene, q is 0 or 1, $X^4$ is selected from a covalent bond or a divalent linking group including —O—, —O—CO—, —O—CO—NH—, —S—, —NH—, —NH—CO—, —NH—CO—NH, —NH—CO—O—, —O—CO—NH and $R^{RI*}$ is a high refractive index group.

As will be understood, functionalization with the compounds of Formulas VIa,b will yield pendent high refractive index groups with the linking group $Y^{1*}$ or $Y^{2*}$, where $Y^{1*}$ or $Y^{2*}$ represents the inking groups resulting from reaction between the electrophilic and nucleophilic functional groups.

Useful $Y^1$ and $Y^2$ groups of compounds of formula VIa,b include hydroxyl, amino, oxazolinyl, oxazolonyl, acetyl, acetonyl, carboxyl, isocyanato, epoxy, aziridinyl, acyl halide, halide and cyclic anhydride groups. Where the reactive functional group $X^2$ is an isocyanato functional group, the co-reactive functional $Y^2$ group preferably comprises a amino or hydroxyl group. Where the pendent reactive functional group $X^2$ comprises a hydroxyl group, the co-reactive functional group $Y^1$ preferably comprises a carboxyl, ester, acyl halide, isocyanato, epoxy, anhydride, azlactonyl or oxazolinyl group. Where the pendent reactive functional group comprises a $X^2$ carboxyl group, the co-reactive functional $Y^2$ group preferably comprises a hydroxyl, amino, epoxy, isocyanate, or oxazolinyl group.

Useful high refractive functional groups include benzyl, 2-, 3-, and 4-biphenyl, 1-, 2, 3-, 4-, and 9-fluorenyl, 4-(1-methyl-1-phenethyl)phenoxyethyl; phenylthio; 1-, 2-, 3- and 4-napthyl, 1- and 2-naphthylthio; 2,4,6-tribromophenoxy; 2,4-dibromophenoxy; 2-bromophenoxy; 1-, and 2-naphthyloxy; 3-phenoxy-; 2-, 3- and 4-phenylphenoxy; 2,4-dibromo-6-sec-butylphenyl; 2,4-dibromo-6-isopropylphenyl; 2,4-dibromophenyl; pentabromobenzyl and pentabromophenyl.

In certain embodiments the functional groups $Y^1$ and $Y^2$ may be connected to the high refractive index group $R^{RI*}$ by a covalent bond ($X^4$ is "—") and subscript q is 0. The intermediate can be provided with the requisite ethylenically unsaturated group and high refractive index group in any sequence, or simultaneously, provided the additional fragmentation oligomer of Formula I results. In the following simplified Scheme, a hydroxyl-functional intermediate of the oligomer of Formula I is functionalized with the high refractive index group.

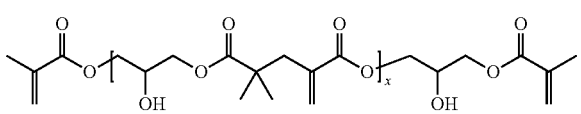

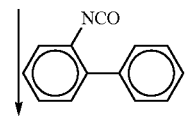

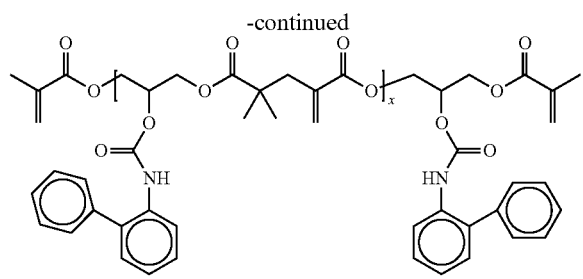

The present disclosure further provides a polymerizable composition comprising the addition-fragmentation oligomer of Formula I, and at least one polymerizable monomer, such as (meth)acryloyl monomers, including acrylate esters, amides, and acids to produce (meth)acrylate homo- and copolymers. Generally, the addition-fragmentation oligomer of Formula I is used in amounts of 0.1 to 10 parts by weight, preferably 0.1 to 5 parts by weight, based on 100 parts by weight of total monomer.

The (meth)acrylate ester monomer useful in preparing the (meth)acrylate polymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth) acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctyl-alcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable source, such as 2-octanol, citronellol, or dihydrocitronellol.

In some embodiments it is desirable for the (meth)acrylic acid ester monomer to include a high $T_g$ monomer. The homopolymers of these high $T_g$ monomers have a $T_g$ of at least 25° C., and preferably at least 50° C. Examples of suitable monomers useful in the present invention include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

The (meth)acrylate ester monomer is present in an amount of up to 100 parts by weight, preferably 85 to 99.5 parts by weight based on 100 parts total monomer content used to prepare the polymer, exclusive of the amount of multifunctional (meth)acrylates. Preferably (meth)acrylate ester monomer is present in an amount of 90 to 95 parts by weight based on 100 parts total monomer content. When high $T_g$ monomers are included, the copolymer may include up to 50 parts by weight, preferably up to 20 parts by weight of the (meth)acrylate ester monomer component.

The polymer may further comprise an acid functional monomer, where the acid functional group may be an acid per se, such as a carboxylic acid, or a portion may be a salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic or phosphoric acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer is generally used in amounts of 0.5 to 15 parts by weight, preferably 1 to 15 parts by weight, most preferably 5 to 10 parts by weight, based on 100 parts by weight total monomer.

The polymer may further comprise a polar monomer. The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono (meth)acrylates; alkyl vinyl ethers, including vinyl methyl ether; and mixtures thereof. Preferred polar monomers include those selected from the group consisting of 2-hydroxyethyl (meth)acrylate and N-vinylpyrrolidinone. The polar monomer may be present in amounts of 0 to 10 parts by weight, preferably 0.5 to 5 parts by weight, based on 100 parts by weight total monomer.

The polymer may further comprise a vinyl monomer. When used, vinyl monomers useful in the (meth)acrylate polymer include vinyl esters (e.g., vinyl acetate and vinyl propionate), styrene, substituted styrene (e.g., α-methyl styrene), vinyl halide, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight total monomer.

A multifunctional (meth)acrylate may be incorporated into the blend of polymerizable monomers. Examples of useful multifunctional (meth)acrylates include, but are not limited to, di(meth)acrylates, tri(meth)acrylates, and tetra (meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth) acrylate is tailored depending upon application of the adhesive composition, for example, adhesives, hardcoats or dental resins. Typically, the multifunctional (meth)acrylate is present in amounts up to 100 parts based on the weight of remaining polymerizable composition. In some embodiments the multifunctional (meth)acrylate is used in amounts of 50 parts by weight or more, based on the weight of remaining polymerizable composition. In some embodiments, the crosslinker may be present in amounts from 0.01 to 5 parts, preferably 0.05 to 1 parts, based on 100 parts total monomers of the adhesive composition for adhesive applications, and greater amounts for hardcoats or dental resins, as described herein.

In such embodiments, the copolymer may comprise:
i. up to 100 parts by weight, preferably 85 to 99.5 parts by weight of an (meth)acrylic acid ester;
ii. 0 to 15 parts by weight, preferably 0.5 to 15 parts by weight of an acid functional ethylenically unsaturated monomer;
iii. 0 to 15 parts by weight of a non-acid functional, ethylenically unsaturated polar monomer;
iv. 0 to 5 parts vinyl monomer;
v. 0 to 100 parts of a multifunctional (meth)acrylate, relative to i-iv;
vi. 0 to 5 parts of a polymerizable photoinitiator. based on 100 parts by weight total monomer.

The composition may be polymerized with either a thermal initiator or photoinitiator. Any conventional free radical initiator may be used to generate the initial radical. Examples of suitable thermal initiators include peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, Del.) under the VAZO trade designation including VAZO™ 67 (2,2'-azo-bis(2-methybutyronitrile)) VAZO™ 64 (2,2'-azo-bis(isobutyronitrile)) and VAZO™ 52 (2,2'-azo-bis(2,2-dimethyvaleronitrile)), and Lucidol™ 70 from Elf Atochem North America, Philadelphia, Pa.

Useful photoinitiators include benzoin ethers such as benzoin methyl ether and benzoin isopropyl ether; substituted acetophenones such as 2, 2-dimethoxyacetophenone, available as Irgacure™ 651 photoinitiator (Ciba Specialty Chemicals), 2,2 dimethoxy-2-phenyl-1-phenylethanone, available as Esacure™ KB-1 photoinitiator (Sartomer Co.; West Chester, Pa.), and dimethoxyhydroxyacetophenone; substituted α-ketols such as 2-methyl-2-hydroxy propiophenone; aromatic sulfonyl chlorides such as 2-naphthalenesulfonyl chloride; and photoactive oximes such as 1-phenyl-1,2-propanedione-2-(O-ethoxy-carbonyl)oxime.
Particularly preferred among these are the substituted acetophenones.

The initiator is used in an amount effective to facilitate free radical addition to the addition-fragmentation crosslinking oligomer and the amount will vary depending upon, e.g., the type of initiator, and the molecular weight of the polymer and the degree of functionalization desired. The initiators can be used in amounts from about 0.001 part by weight to about 5 parts by weight based on 100 parts total monomer.

The curable composition may also include other additives. Examples of suitable additives include tackifiers (e.g., rosin esters, terpenes, phenols, and aliphatic, aromatic, or mixtures of aliphatic and aromatic synthetic hydrocarbon resins), surfactants, plasticizers (other than physical blowing agents), nucleating agents (e.g., talc, silica, or $TiO_2$), pigments, dyes, reinforcing agents, solid fillers, stabilizers (e.g., UV stabilizers), and combinations thereof. The additives may be added in amounts sufficient to obtain the desired properties for the cured composition being produced. The desired properties are largely dictated by the intended application of the resultant polymeric article.

Adjuvants may optionally be added to the compositions such as colorants, abrasive granules, anti-oxidant stabilizers, thermal degradation stabilizers, light stabilizers, conductive particles, tackifiers, flow agents, bodying agents, flatting agents, inert fillers, binders, blowing agents, fungicides, bactericides, surfactants, plasticizers, rubber tougheners and other additives known to those skilled in the art. They also can be substantially unreactive, such as fillers, both inorganic and organic. These adjuvants, if present, are added in an amount effective for their intended purpose.

In some embodiments, a toughening agent may be used. The toughening agents which are useful in the present invention are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski), incorporated herein by reference. Preferable rubbery backbones comprise polymerized butadiene or a polymerized mixture of butadiene and styrene. Preferable shells comprising polymerized methacrylic acid esters are lower alkyl ($C_1$-$C_4$) substituted methacrylates. Preferable monovinyl aromatic hydrocarbons are styrene, alphamethylstyrene, vinyltoluene, vinylxylene, ethylvinylbenzene, isopropylstyrene, chlorostyrene, dichlorostyrene, and ethylchlorostyrene. It is important that the graft copolymer contain no functional groups that would poison the catalyst.

Examples of useful toughening agents of the second type are acrylate core-shell graft copolymers wherein the core or backbone is a polyacrylate polymer having a glass transition temperature below about 0° C., such as polybutyl acrylate or polyisooctyl acrylate to which is grafted a polymethacrylate polymer (shell) having a glass transition above about 25° C., such as polymethylmethacrylate.

The third class of toughening agents useful in the invention comprises elastomeric particles that have a glass transition temperature ($T_g$) below about 25° C. before mixing with the other components of the composition. These elastomeric particles are polymerized from free radical polymerizable monomers and a copolymerizable polymeric stabilizer that is soluble in the resins. The free radical polymerizable monomers are ethylenically unsaturated monomers or diisocyanates combined with coreactive difunctional hydrogen compounds such as diols, diamines, and alkanolamines.

Useful toughening agents include core/shell polymers such as methacrylate-butadiene-styrene (MBS) copolymer wherein the core is crosslinked styrene/butadiene rubber and the shell is polymethylacrylate (for example, ACRYLOID KM653 and KM680, available from Rohm and Haas, Philadelphia, Pa.), those having a core comprising polybutadiene and a shell comprising poly(methyl methacrylate) (for example, KANE ACE M511, M521, B11A, B22, B31, and M901 available from Kaneka Corporation, Houston, Tex. and CLEARSTRENGTH C223 available from ATOFINA, Philadelphia, Pa.), those having a polysiloxane core and a polyacrylate shell (for example, CLEARSTRENGTH S-2001 available from ATOFINA and GENIOPERL P22 available from Wacker-Chemie GmbH, Wacker Silicones, Munich, Germany), those having a polyacrylate core and a poly(methyl methacrylate) shell (for example, PARALOID EXL2330 available from Rohm and Haas and STAPHY-LOID AC3355 and AC3395 available from Takeda Chemical Company, Osaka, Japan), those having an MBS core and a poly(methyl methacrylate) shell (for example, PARAL-OID EXL2691A, EXL2691, and EXL2655 available from Rohm and Haas) and the like and mixtures thereof. Preferred modifiers include the above-listed ACRYLOID and PARALOID modifiers and the like, and mixtures thereof.

The toughening agent is useful in an amount equal to about 1-35%, preferably about 3-25%, based on the weight of the curable composition. The toughening agents of the instant invention add strength to the composition after curing without reacting with the component of the curable composition or interfering with curing.

In some embodiments, the partially cured composition may be disposed between two substrates (or adherends), and subsequently fully cured to effect a structural or semistructual bond between the substrates. Therefore the present disclosure provides structural and semi-structural adhesives. "Semi-structural adhesives" are those cured adhesives that have an overlap shear strength of at least about 0.5 MPa, more preferably at least about 1.0 MPa, and most preferably at least about 1.5 MPa. Those cured adhesives having particularly high overlap shear strength, however, are referred to as structural adhesives. "Structural adhesives" are those cured adhesives that have an overlap shear strength of at least about 3.5 MPa, more preferably at least about 5 MPa, and most preferably at least about 7 MPa.

Fillers

In some embodiments the crosslinkable composition may include filler. In some embodiments the total amount of filler is at most 50 wt. %, preferably at most 30 wt. %, and more preferably at most 10 wt. % filler. Fillers may be selected from one or more of a wide variety of materials, as known in the art, and include organic and inorganic filler. Inorganic filler particles include silica, submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

In some embodiments the filler may be surface modified. A variety of conventional methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. No. 2,801,185 (Iler), U.S. Pat. No. 4,522,958 (Das et al.) U.S. Pat. No. 6,586,483 (Kolb et al.), each incorporated herein by reference.

Surface-modifying groups may be derived from surface-modifying agents. Schematically, surface-modifying agents can be represented by the formula X—Y, where the X group is capable of attaching to the surface of the particle (i.e., the silanol groups of a silica particle) and the Y group is a reactive or non-reactive functional group. A non-functional group does not react with other components in the system (e.g. the substrate). Non-reactive functional groups can be selected to render the particle relatively more polar, relatively less polar or relatively non-polar. In some embodiments the non-reactive functional group "B" is a hydrophilic group such as an acid group (including carboxylate, sulfonate and phosphonate groups), ammonium group or poly (oxyethylene) group, or hydroxyl group. In other embodiments, "B" may be a reactive functional groups such as an ethylenically unsaturated polymerizable group, including vinyl, allyl, vinyloxy, allyloxy, and (meth)acryloyl, that may be free-radically polymerized with the polymerizable resin or monomers.

Such optional surface-modifying agents may be used in amounts such that 0 to 100%, generally 1 to 90% (if present) of the surface functional groups (Si—OH groups) of the silica nanoparticles are functionalized. The number of functional groups is experimentally determined where quantities of nanoparticles are reacted with an excess of surface modifying agent so that all available reactive sites are functionalized with a surface modifying agent. Lower percentages of functionalization may then be calculated from the result. Generally, the amount of surface modifying agent is used in amount sufficient to provide up to twice the equal weight of surface modifying agent relative to the weight of inorganic nanoparticles. When used, the weight ratio of surface modifying agent to inorganic nanoparticles is preferably 2:1 to 1:10. If surface-modified silica nanoparticles are desired, it is preferred to modify the nanoparticles prior to incorporation into the coating composition.

In some embodiments the surface modified filler may be selected from the addition-fragmentation agent modified filers as described in Applicant's copending publication no. WO 2013/028397 and WO 2014/074427, each incorporated herein by reference.

The present addition fragmentation oligomers are also useful in the preparation of hardcoats. The term "hardcoat" or "hardcoat layer" means a layer or coating that is located on the external surface of an object, where the layer or coating has been designed to at least protect the object from abrasion. The present disclosure provides hardcoat compositions comprising the addition-fragmentation oligomer of Formula I and, a multi-functional (moth)acrylate monomer comprising three or more (meth)acrylate groups, and/or a multi-functional (meth)acrylate oligomer and optionally a (meth)acrylate-functional diluent.

Useful multifunctional (meth)acrylate monomers comprise three or more (meth)acrylate groups. Multifunctional (meth)acrylate monomers are useful in the practice of the present invention because they add abrasion resistance to the hard coat layer. Preferred multifunctional (meth)acrylate monomers comprising three or more (meth)acrylate groups include trimethylol propane tri(meth)acrylate (TMPTA), pentaerythritol tri(meth)acrylate, pentaerythritol tetra(meth) acrylate, dipentrithritol tri(meth)acrylate (Sartomer 355), dipentaerythritol penta(meth)acrylate (Sartomer 399), dipentaerythritol hydroxy penta(meth)acrylate (DPHPA), glyceryl propoxy tri(meth)acrylate, trimethylopropane tri (meth)acrylate, and mixtures thereof Another useful radiation-curable component of the present invention is the class of multifunctional (meth)acrylate oligomers, having two or more (meth)acrylate groups, and having an average molecular weight ($M_w$) in the range from about 400 to 2000.

Useful multi-functional (meth)acrylate oligomers include polyester (meth)acrylates, polyurethane (meth)acrylates, and (meth)acrylated epoxy (meth)acrylates. (Meth)acrylated epoxy (meth)acrylates and polyester(meth)acrylates are most preferred because they tend to have a relatively low viscosity and therefore allow a more uniform layer to be applied by the spin coating method. Specifically, preferred multifunctional (meth)acrylate oligomers include those commercially available from UCB Radcure, Inc. of Smyrna, Ga. and sold under the trade name Ebecryl (Eb): Eb40 (tetrafunctional acrylated polyester oligomer), ENO (polyester tetra-functional (meth)acrylate oligomer), Eb81 (multifunctional (meth)acrylated polyester oligomer), Eb600 (bisphenol A epoxy di(meth)acrylate), Eb605 (bisphenol A epoxy di(meth)acrylate diluted with 25% tripropylene glycol di(meth)acrylate), Eb639 (novolac polyester oligomer), Eb2047 (trifunctional acrylated polyester oligomer), Eb3500 (di-functional Bisphenol-A oligomer acrylate), Eb3604 (multi-functional polyester oligomer acrylate), Eb6602 (trifunctional aromatic urethane acrylate oligomer), Eb8301 (hexafunctional aliphatic urethane acrylate), EbW2 (difunctional aliphatic urethane acrylate oligomer), and mixtures thereof. Of these, the most preferred are, Eb 600, Eb605, Eb80, and Eb81.

The (meth)acrylate-functional diluents, also referred to herein as "reactive diluents", are relatively low molecular weight mono- or di-functional, non-aromatic, (meth)acrylate monomers. These relatively low molecular weight reactive diluents are advantageously of a relatively low viscosity, e.g., less than about 30 centipoise (cps) at 25 C. Di-functional, non-aromatic (meth)acrylates are generally preferred over monofunctional non-aromatic (meth)acrylates because di-functional non-aromatic (meth)acrylates allow for quicker cure time. Preferred reactive diluents include 1,6-hexanediol di(meth)acrylate (HDDA from UCB Radcure, Inc. of Smyrna, Ga.), tripropylene glycol di(meth) acrylate, isobornyl (meth)acrylate (1130A, Radcure), 2(2-ethoxyethoxy) ethyl (meth)acrylate (sold under the trade name Sartomer 256 from SARTOMER Company, Inc. of Exton, Pa.), n-vinyl formamide (Sartomer 497), tetrahydrofurfuryl (meth)acrylate(Sartomer 285), polyethylene glycol di(meth)acrylate (Sartomer 344), tripropylene glycol di(meth)acrylate (Radcure), neopentyl glycol dialkoxy di(meth) acrylate, polyethyleneglycol di(meth)acrylate, and mixtures thereof.

The hardcoat composition may comprise:

0.1-10 wt. % of the addition fragmentation oligomer of Formula I;

20-80 wt. % of multifunctional (meth)acrylate monomers and/or multifunctional (meth)acrylate oligomers, 0 to 25 wt. % range of (meth)acrylate diluent, (0-25 wt. %)

20 to 75 wt. % of silica. The weight ranges referring to the silica per se, whether or not functionalized.

In some embodiments the amount of silica, including the silica modified with conventional surface modifying oligomers and unmodified silica is 20-75 wt. %, preferably 50-70 wt. %.

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

The present disclosure further provides curable dental compositions comprising the addition-fragmentation oligomer of Formula I. Although various curable dental compositions have been described, industry would find advantage in compositions having improved properties such as reduced stress deflection and/or reduced shrinkage while maintaining sufficient mechanical properties and depth of cure.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein:

"dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"curable" is descriptive of a material or composition that can be polymerized or crosslinked by a free-radical means such as by irradiating with actinic irradiation to induce polymerization and/or crosslinking; "hardened" refers to a material or composition that has been cured (e.g., polymerized or crosslinked).

"initiator" refers to something that initiates curing of a resin. An initiator may include, for example, a polymerization initiator system, a photoinitiator system, a thermal initiator and/or a redox initiator system.

"self-etching" composition refers to a composition that bonds to a dental structure surface without pretreating the dental structure surface with an etchant. Preferably, a self-etching composition can also function as a self-primer wherein no separate etchant or primer are used.

a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

a "dental structure surface" refers to tooth structures (e.g., enamel, dentin, and cementum) and bone.

an "uncut" dental structure surface refers to a dental structure surface that has not been prepared by cutting, grinding, drilling, etc.

an "untreated" dental structure surface refers to a tooth or bone surface that has not been treated with an etchant, primer, or bonding agent prior to application of a self-etching adhesive or a self-adhesive composition of the present invention.

an "unetched" dental structure surface refers to a tooth or bone surface that has not been treated with an etchant prior to application of a self-etching adhesive or a self-adhesive composition of the present invention.

The total amount of addition-fragmentation oligomer(s) in the polymerizable resin portion of the unfilled curable dental composition is typically no greater than 15 wt. %. As the concentration of the addition-fragmentation monomer increases, the stress deflection and Watts Shrinkage typically decrease. However, when the amount of addition-fragmentation oligomer exceeds an optimal amount, mechanical properties such as Diametral tensile strength and/or Barcol hardness, or depth of cure may be insufficient.

The polymerizable resin portion of the curable dental composition described herein comprises at least 0.1 wt. %, of addition-fragmentation oligomer(s). Generally, the amount of addition-fragmentation oligomer is from about 0.5 to 10 wt. % of the polymerizable portion of the unfilled dental composition.

The filled curable dental composition described herein typically comprises at least 0.1 wt. %, of addition-fragmentation oligomer(s). The total amount of addition-fragmentation oligomer(s) in the filled curable dental composition is typically no greater than 5 wt. %.

Materials with high polymerization stress upon curing generate strain in the tooth structure. One clinical consequence of such stress can be a decrease in the longevity of the restoration. The stress present in the composite passes through the adhesive interface to the tooth structure generating cuspal deflection and cracks in the surrounding dentin and enamel which can lead to postoperative sensitivity as described in R. R. Cara et al, Particulate Science and Technology 28; 191-206 (2010). Preferred (e.g. filled) dental compositions (useful for restorations such as fillings and crowns) described herein typically exhibit a stress deflection of no greater than 4.0, or 3.0, or 2.0, or 1.0 microns.

The curable compositions described herein further comprise at least one ethylenically unsaturated resin monomer or oligomer in combination with the addition-fragmentation oligomer. In some embodiments, such as primers, the ethylenically unsaturated monomer may be monofunctional, having a single (e.g. terminal) ethylenically unsaturated group. In other embodiments, such as dental restorations the ethylenically unsaturated monomer is multifunctional. The phrase "multifunctional ethylenically unsaturated" means that the monomers each comprise at least two ethylenically unsaturated (e.g. free radically) polymerizable groups, such as (meth)acrylate groups.

The amount of curable resin in the dental composition is a function of the desired end use (adhesives, cements, restoratives, etc.) and can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

In favored embodiments, such ethylenically unsaturated groups of the curable dental resin includes (meth)acryloyl such as (meth)acrylamide and (meth)acrylate. Other ethylenically unsaturated polymerizable groups include vinyl and vinyl ethers. The ethylenically unsaturated terminal polymerizable group(s) is preferably a (meth)acrylate group, particularly for compositions that are hardened by exposure to actinic (e.g. UV and visible) radiation. Further, methacrylate functionality is typically preferred over the acrylate functionality in curable dental compositions. The ethylenically unsaturated monomer may comprise various ethylenically unsaturated monomers, as known in the art, for use in dental compositions.

In favored embodiments, the (e.g. dental) composition comprises one or more dental resins having a low volume shrinkage monomer. Preferred (e.g. filled) curable dental compositions (useful for restorations such as fillings and crowns) comprise one or more low volume shrinkage resins such that the composition exhibits a Watts Shrinkage of less than about 2%.

Preferred low volume shrinkage monomers include isocyanurate resins, such as described in U.S.S.N. 2011/027523 (Abuelyaman et al.); tricyclodecane resins, such as described in U.S.S.N 2011/041736; polymerizable resins having at least one cyclic allylic sulfide moiety such as described in U.S. Pat. No. 7,888,400 (Abuelyaman et al.); methylene dithiepane silane resins as described in U.S. Pat. No. 6,794,520 (Moszner et al.); and di-, tri, and/or tetra-(meth)acryloyl-containing resins such as described in U.S. 2010/021869 (Abuelyaman et al.); each of which are incorporated herein by reference.

In favored embodiments, the majority of the (e.g. unfilled) polymerizable resin composition comprises one or more low volume shrinkage monomers ("Low shrinkage monomers"). For example, at least 50%, 60%, 70%, 80%, 90% or more of the (e.g. unfilled) polymerizable resin may comprise low volume shrinkage monomer(s).

In one embodiment, the dental composition comprises at least one isocyanurate resin. The isocyanurate resin comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated (e.g. free radically) polymerizable groups are generally bonded to the core or backbone unit via a (e.g. divalent) linking group.

The trivalent isocyanurate core structure generally has the formula:

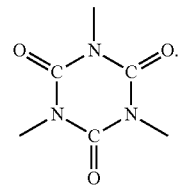

The divalent linking group comprises at least one nitrogen, oxygen or sulfur atom. Such nitrogen, oxygen or sulfur atom forms an urethane, ester, thioester, ether, or thioether linkage. Ether and especially ester linkages can be beneficial over isocyanurate resin comprising urethane linkages for providing improved properties such as reduced shrinkage, and/or increased mechanical properties, e.g., diametral tensile strength (DTS). Thus, in some embodiments, the divalent linking groups of the isocyanurate resin are free of urethane linkages. In some favored embodiments, the divalent linking group comprises an ester linkage such as an aliphatic or aromatic diester linkage.

The isocyanurate monomer typically has the general structure:

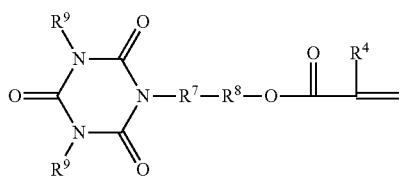

wherein $R^7$ is a (hetero)hydrocarbyl group including straight chain, branched or cyclic alkylene, arylene, or alkarylene, and optionally including a heteroatom (e.g. oxygen, nitrogen, or sulfur); $R^4$ is hydrogen or C1-C4 alkyl; $R^8$ is heterohydrocarbyl group including alkylene, arylene, or alkarylene linking group comprising at least one moiety selected from urethane, ester, thioester, ether, or thioether, and combinations of such moieties; and at least one of the $R^9$ groups is

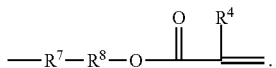

$R^7$ is typically a straight chain, branched or cyclic alkylene, optionally including a heteroatom, having no greater than 12 carbons atoms. In some favored embodiments, $R^7$ has no greater than 8, 6, or 4 carbon atoms. In some favored embodiments, $R_7$ comprises at least one hydroxyl moiety.

In some embodiments, $R^8$ comprises an aliphatic or aromatic ester linkage such as a diester linkage.

In some embodiment, $R^8$ further comprises one or more ether moieties. Hence, the linking group may comprise a combination of ester or diester moieties and one or more ether moieties.

For embodiments, wherein the isocyanurate monomer is a di(meth)acrylate monomer, $R^9$ is hydrogen, alkyl, aryl, or alkaryl, optionally including a heteroatom.

The polymerizable resin portion of the curable unfilled dental composition described herein may comprise at least 10 wt. %, 15 wt. %, 20 wt. %, or 25 wt. %, multifunctional ethylenically unsaturated isocyanurate resin(s). The isocyanurate resin may comprise a single monomer or a blend of two or more isocyanurate resins. The total amount of isocyanurate resin(s) in the unfilled polymerizable resin portion of the curable dental composition is typically no greater than 90 wt. %, 85 wt. %, 80 wt. %, or 75 wt. %.

The filled curable dental composition described herein typically comprises at least 5 wt. %, 6 wt. %, 7 wt. %, 8 wt. %, or 9 wt. % of multifunctional ethylenically unsaturated isocyanurate resin(s). The total amount of isocyanurate resin(s) of the filled hardenable (i.e. polymerizable) dental composition is typically no greater than 20 wt. %, or 19 wt. %, or 18 wt. %, or 17 wt. %, or 16 wt. %, or 15 wt. %.

In another embodiment, the dental composition comprises at least one tricyclodecane resin. The tricyclodecane resin may comprise a single monomer or a blend of two or more tricyclodecane resins. The concentration of multifunctional ethylenically unsaturated tricyclodecane monomer in the (i.e. unfilled) polymerizable resin portion or filled hardenable (i.e. polymerizable) composition can be the same as just described for the multifunctional ethylenically unsaturated isocyanurate monomer.

Tricyclodecane monomers generally have the core structure (i.e. backbone unit (U)):

The backbone unit (U) if the tricyclodecane resin typically comprises one or two spacer unit(s) (S) bonded to the backbone unit (U) via an ether linkage. At least one spacer unit (S) comprises a CH(R10)-OG chain, wherein each group G comprises a (meth)acrylate moiety and R10 (comprises at least one group selected from hydrogen, alkyl, aryl, alkaryl and combinations thereof. In some embodiments, R10 is hydrogen, methyl, phenyl, phenoxymethyl, and combinations thereof. G may be bonded to the spacer unit(s) (S) via a urethane moiety.

In some embodiments, the spacer unit(s) (S) typically comprise

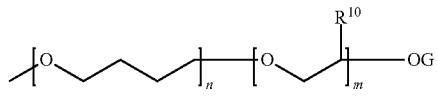

wherein m is 1 to 3; n is 1 to 3; and $R^{10}$ is hydrogen, methyl, phenyl, phenoxymethyl.

In other embodiments, the spacer unit(s) (S) typically comprise

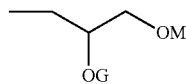

wherein M=aryl.

In some embodiments the composition comprises a multifunctional ethylenically unsaturated isocyanurate monomer and multifunctional ethylenically unsaturated tricyclodecane monomer at a weight ratio ranging from about 1.5:1 to 1:1.5.

In some embodiments, the curable dental composition comprises a polymerizable resin having at least one cyclic allylic sulfide moiety with at least one (meth)acryloyl moiety.

The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth)acrylate moiety) or a (meth) acryloylamino (i.e., a (meth)acrylamide moiety).

In one embodiment, the low shrinkage resin includes those represented by the formulae:

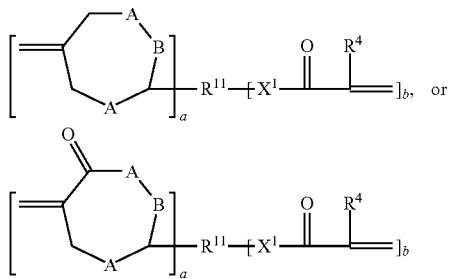

In the above formulae, each A can be independently selected from S, O, N, C (e.g., $C(R^{10})_2$, where each $R^{10}$ is independently a H or an organic group), SO, $SO_2$, N-alkyl, N-acyl, NH, N-aryl, carboxyl or carbonyl group, provided that at least one X is S or a group comprising S. Preferably, each A is sulfur.

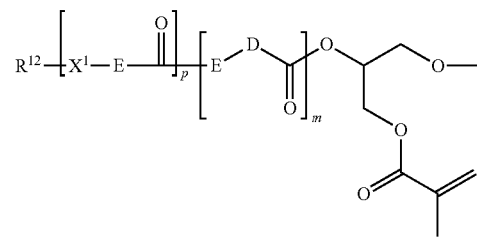

B is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

$X^1$ is independently —O— or —$NR^4$—, where $R^4$ is H or $C_1$-$C_4$ alkyl.

The $R^{11}$ group represents a linker selected from alkylene (typically having more than one carbon atom, i.e. excluding methylene), alkylene optionally including a heteroatom (e.g., O, N, S, S—S, SO, $SO_2$), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

$R^4$ is H or $C_1$-$C_4$ alkyl, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC (O)—). Typically the weight average molecular weight (MW) of the hybrid monomer ranges from about 400 to about 900 and in some embodiments is at least 250, more typically at least 500, and most typically at least 800.

The inclusion of a polymerizable compound having at least one cyclic allylic sulfide moiety can result in a synergistic combination of low volume shrinkage in combination with high diametral tensile strength.

In another embodiment, the dental composition comprises a low shrinkage resin that includes at least one di-, tri-, and/or tetra (meth)acryloyl-containing resins having the general formula:

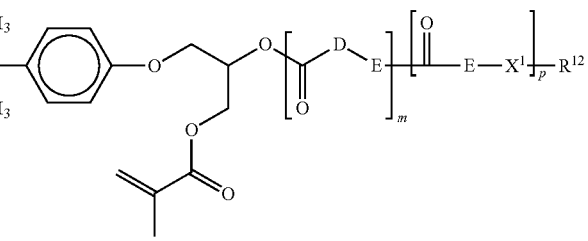

wherein: each $X^1$ is independently —O— or —$NR^4$—, where $R^4$ is H or $C_1$-$C_4$ alkyl;
D and E each independently represent an organic group, and $R^{12}$ represents —$C(O)C(CH_3)=CH_2$, and/or p=0 and $R^{12}$ represents H, —$C(O)CH=CH_2$, or —$C(O)C(CH_3)=CH_2$, with the proviso that at least one $R^{12}$ is a (meth)acrylate; each m is 1 to 5; p and q are independently 0 or 1. Although, this material is a derivative of bisphenol A, when other low volume shrinkage monomer are employed, such as the isocyanurate and/or tricyclodecane monomer, the dental composition is free of (meth)acrylate monomers derived from bisphenol A. Such resins are described in WO 2008/082881 (Abuelyaman et al.)

In another embodiment, the low shrinkage dental resin may be selected from methylene dithiepane silane resins described in U.S. Pat. No. 6,794,520 (Moszner et al.), incorporated herein by reference. Such resins have the general formula

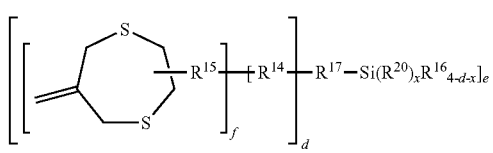

in which $R^{14}$ is a saturated or unsaturated aliphatic or alicyclic hydrocarbon radical with 1 to 10 carbon atoms, which can be interrupted by one or more oxygen and/or sulfur atoms and can contain one or more ester, carbonyl, amide and/or urethane groups, or is an aromatic or heteroaromatic hydrocarbon radical with 6 to 18 carbon atoms, the hydrocarbon radicals being able to be substituted or unsubstituted; $R^{15}$ has one of the meanings given for $R^{14}$ or is absent; $R^{16}$ has one of the meanings given for $R^{14}$ or is absent; $R^{17}$ is equal to —$(CHR^{19})_n$—, —W—CO—NH—$(CHR^{19})_n$—, —Y—CO—NH—$R^{18}$—, —$(CHR^{19})_n$, —$SR^{18}$—, —CO—O—$R^{18}$— or is absent, with n being equal to 1 to 4, $R^{19}$ is hydrogen, $C_1$ to $C_{10}$ alkyl or $C_6$ to $C_{10}$ aryl, $R^{18}$ has one of the meanings given for $R^{14}$ and W stands for an O or S atom or is absent; with $R^{18}$ and $R^{19}$ being able to be substituted or unsubstituted; $R^{20}$ is a hydrolyzable group; d, e, f and x each independently of each other being 1, 2 or 3; and the sum of d+x=2 to 4.

The multifunctional low shrink resins are (e.g. highly) viscous liquids at about 25° C., yet are flowable. The viscosity as can be measured with a Haake RotoVisco RV1 device, as described in US 2013/0109777 (Eckert et al.) is typically at least 300, or 400, or 500 Pa*s and no greater than 10,000 Pascal-seconds (Pa*s). In some embodiments, the viscosity is no greater than 5000 or 2500 Pa*s.

The ethylenically unsaturated resins of the dental composition are typically stable liquids at about 25° C. meaning that the resins do not substantially polymerize, crystallize, or otherwise solidify when stored at room temperature (about 25° C.) for a typical shelf life of at least 30, 60, or 90 days. The viscosity of the resins typically does not change (e.g. increase) by more than 10% of the initial viscosity.

Particularly for dental restoration compositions, the ethylenically unsaturated resins generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight resin lacking such substituents).

In some embodiments, the (unfilled) polymerizable resin may comprise solely one or more low shrink resins in combination with the addition fragmentation oligomer(s). In other embodiments, the (unfilled) polymerizable resin comprises a small concentration of other monomer(s). By "other" is it meant an ethylenically unsaturated monomer such as a (meth)acrylate monomer that is not a low volume shrinkage monomer.

The concentration of such other monomer(s) is typically no greater than 20 wt. %, 19 wt. %, 18 wt. %, 17 wt. %, 16 wt. %, or 15 wt. % of the (unfilled) polymerizable resin portion. The concentration of such other monomers is typically no greater than 5 wt. %, 4 wt. %, 3 wt. %, or 2 wt. % of the filled polymerizable dental composition.

In some embodiments, the "other monomers" of the dental composition comprise a low viscosity reactive (i.e. polymerizable) diluent. Reactive diluents typically have a viscosity of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers.

In some embodiments, the reactive diluent is an isocyanurate or tricyclodecane monomer. Tricyclodecane reactive diluent may have the same generally structure as previously described. In favored embodiments, the tricyclodecane reactive diluent comprises one or two spacer unit(s) (S) being connected to the backbone unit (U) via an ether linkage; such as described in US 2011/041736 (Eckert et al.); incorporated herein by reference.

Although the inclusion of an addition fragmentation oligomer in a low volume shrinkage composition typically provides the lowest stress and/or lowest shrinkage, the addition fragmentation oligomers described herein can also reduce the stress of dental composition comprising conventional hardenable (meth)acrylate monomers, such as ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethyleneglycol dimethacrylate, neopentylglycol dimethacrylate (NPGDMA), and polyethyleneglycol dimethacrylate (PEGDMA).

The curable component of the curable dental composition can include a wide variety of "other" ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof.

Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups as an example of an "other monomer". Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are available from a wide variety of commercial sources, such as Sigma-Aldrich, St. Louis.

The curable dental compositions can include at least 1 wt. %, at least 3 wt. %, or at least 5 wt. % ethylenically unsaturated compounds with hydroxyl functionality, based on the total weight of the unfilled composition. The compositions can include at most 80 wt. %, at most 70 wt. %, or at most 60 wt. % ethylenically unsaturated compounds with hydroxyl functionality.

The dental compositions described herein may include one or more curable components in the form of ethylenically unsaturated compounds with acid functionality as an example of an "other" monomer. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron. Such acid-functional "other" monomers contribute to the self-adhesion or self-etching of the dental compositions as described in U.S. 2005/017966 (Falsafi et al.), incorporated herein by reference.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, $\alpha,\beta$-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components. Also monomers, oligomers, and polymers of unsaturated carbonic acids such as (meth)acrylic acids, itaconic acid, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_1$-$C_4$ hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_5$-$C_{12}$ hydrocarbon group; an ethylenically unsaturated compound without acid functionality; an initiator system; and a filler.

The curable dental compositions can include at least 1 wt. %, at least 3 wt. %, or at least 5 wt. % ethylenically unsaturated compounds with acid functionality, based on the total weight of the unfilled composition. The compositions can include at most 80 wt. %, at most 70 wt. %, or at most 60 wt. % ethylenically unsaturated compounds with acid functionality.

The curable dental compositions may include resin-modified glass ionomer cements such as those described in U.S. Pat. No. 5,130,347 (Mitra), U.S. Pat. No. 5,154,762 (Mitra), U.S. Pat. No. 5,925,715 (Mitra et al.) and U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the mixture of polymerizable ingredients (i.e. curable resins and the addition-fragmentation oligomer of Formula I). The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

The addition-fragmentation oligomer is generally free-radically cleavable. Although photopolymerization is one mechanism for generating free radicals, other curing mechanisms also generate free radicals. Thus, the addition-fragmentation oligomer does not require irradiation with actinic radiation (e.g. photocuring) in order to provide the reduction in stress during curing.

In some embodiments, the mixture of resins is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroborate. Some preferred photosensitizers may include monoketones and diketones (e.g. alpha diketones) that absorb some light within a range of about 300 nm to about 800 nm (preferably, about 400 nm to about 500 nm) such as camphorquinone, 1-phenyl-1,2-propanedione, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl) phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photoinitiator may also be a polymerizable photoinitiator having a free-radically polymerizable groups and a photoinitiator group. Such polymerizable photoinitiators include 4-benzoylphenyl acrylate, 2-(4-benzoylphenoxy)ethyl acrylate and 2-[4-(2-hydroxy-2-methylpropanoyl)phenoxy]ethyl-N-acryloyl-2-methylalinate, and are described in U.S. Pat. No. 7,838,110 (Zhu et al.), U.S. Pat. No. 5,506,279 (Babu et al.), incorporated herein by reference, and also Temel et al. "Photopolymerization and photophysical properties of amine linked benzophenone photoinitiators for free radical polymerization", Journal of Photochemistry and Photobiology A, Chemistry 219 (2011), pp. 26-31.

The initiator is used in an amount effective to facilitate free radical addition to the addition-fragmentation crosslinking oligomer and the amount will vary depending upon, e.g., the type of initiator and the molecular weight of the polymer and the degree of functionalization desired. The initiators can be used in amounts from about 0.001 part by weight to about 5 parts by weight based on 100 parts total monomer.

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture.

Curing is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 500-1500 mW/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the multifunctional ethylenically unsaturated monomers may be chemically curable, i.e., the compositions contain a chemical initiator (i.e., initiator system) that can polymerize, cure, or otherwise harden the composition without dependence on irradiation with actinic radiation. Such chemically curable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azobisisobutyronitrile, as well as dicumyl peroxide, which is favored for mill blanks.

In favored embodiments, such as when the dental composition is employed as a dental restorative (e.g. dental filling or crown) or an orthodontic cement, the dental composition typically comprises appreciable amounts of (e.g. nanoparticle) filler. The amount of such fillers is a function of the end use as further described herein. Such compositions preferably include at least 40 wt. %, more preferably at least 45 wt. %, and most preferably at least 50 wt. % filler, based on the total weight of the composition. In some embodiments the total amount of filler is at most 90 wt. %, preferably at most 80 wt. %, and more preferably at most 75 wt. % filler.

The (e.g. filled) dental composite materials typically exhibit a diametral tensile strength (DTS) of at least about 70, 75, or 80 MPa and/or a Barcol Hardness of at least about 60, or 65, or 70. The ISO 4049 depth of cure ranges from about 4 to about 5 mm and is comparable to commercially available (e.g. filled) dental compositions suitable for restorations.

Dental compositions suitable for use as dental adhesives can optionally also include filler in an amount of at least 1 wt. %, 2 wt. %, 3 wt. %, 4 wt. %, or 5 wt. % based on the total weight of the composition. For such embodiments, the total concentration of filler is at most 40 wt. %, preferably at most 20 wt. %, and more preferably at most 15 wt. % filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Suitable inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 75 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1041, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO™ 1042 or 2327.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The primary particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like and may comprise silane, zirconate or titanate coupling agents. Preferred coupling agents include gamma-methacryloxypropyltrimethoxysilane, gamma-mercaptopropyltriethoxysilane, gamma-aminopropyltrimethoxysilane, and the like.

Suitable copolymerizable or reactive organometallic compounds may have the general formulas: $CH_2$=$C(R^{22})$—$R^{21}Si(OR)_nR_{3-n}$ or $CH_2$=$C(R^{22})$—$C$=$OOR^{21}Si(OR)_nR_{3-n}$; wherein R is an $C_1$-$C_4$ alkyl, $R^{21}$ is a divalent organic heterohydrocarbyl linking group, preferably alkylene; $R^{22}$ is H or C1-C4 alkyl; and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, the silica particulate filler may be surface modified by an addition-fragmentation oligomer, such as are described in Applicant's copending publication no. WO 2013/028397 and WO 2014-074373 each incorporated herein by reference.

In some embodiments, the disclosure provides a universal restorative composite comprising:
a) 15-30 wt. % of a curable dental resin comprising at least two polymerizable, ethylenically unsaturated groups;
b) 70-85 wt. % of an inorganic filler, preferably a surface modified filler;
c) 0.1 to 10 parts by weight of the addition-fragmentation oligomer, relative to 100 parts by weight of a) and b), said curable composition further comprising an initiator and <2%, stabilizers, pigments, etc.

In some embodiments, the disclosure provides a flowable restorative (flowable) composite comprising:
a) 25-50 wt. % of a curable dental resin comprising at least two polymerizable, ethylenically unsaturated groups;
b) 30-75 wt. % of an inorganic filler, preferably a surface modified filler;
c) 0.1 to 10 parts by weight of the addition-fragmentation oligomer, relative to 100 parts by weight of a) and b), said curable composition further comprising an initiator and <2% initiators, stabilizers, pigments, etc.

In some embodiments, the disclosure provides a resin modified glass-ionomer adhesive comprising:
  a) 10-25 wt. % of a partially (meth)acrylated poly(meth) acrylic acid, which includes acrylic acids such as itaconic acid;
  b) 5-20% of a hydroxyalkyl (meth)acrylate;
  c) 30-60% of fluoroaluminosilicate (FAS) acid reactive glass
  d) 0-20% non-acid reactive fillers, preferably surface-treated;
  e) 10-20% water; and
  f) 0.1 to 10 wt. % of the addition-fragmentation oligomer, relative to 100 parts by weight of a) and b),
  g) said curable composition further comprising an initiator and <2% stabilizers, pigments, etc.

Preferably the floroaluminosilicate is a silane methacrylate surface-treated floroaluminosilicate.

In some embodiments, the disclosure provides a dental adhesive comprising:
a) 30-80 wt. % mono (meth)acrylate monomers;
b) 1-10 wt. % polyfunctional (meth)acrylate monomers;
c) 5-60 wt. %% monomers having a acid-functional group (including phosphate, phosphonate, carboxylate, sulfonic acids)
d) 0-10, preferably 1-10 wt. % poly(meth)acrylic acid methacrylate monomers;
e) 0.1 to 10 wt. % of the addition-fragmentation oligomer, relative to 100 parts by weight of a) to d);
f) an initiator, g) 0-30% inorganic filler, preferably surface modified, relative to 100 parts by weight of a) to d);
h) 0 to 25 wt. % solvent relative to 100 parts by weight of a) to d);
i) 0 to 25 wt. % water relative to 100 parts by weight of a) to d); and <2% stabilizers, pigments, etc.

In some embodiments, the dental compositions can have an initial color different than the cured dental structures. Color can be imparted to the composition through the use of a photobleachable or thermochromic dye. As used herein, "photobleachable" refers to loss of color upon exposure to actinic radiation. The composition can include at least 0.001 wt. % photobleachable or thermochromic dye, and typically at least 0.002 wt. % photobleachable or thermochromic dye, based on the total weight of the composition. The composition typically includes at most 1 wt. % photobleachable or thermochromic dye, and more typically at most 0.1 wt. % photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT,), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be cured into dental articles prior to applying. For example, a dental article such as a crown may be pre-formed from the curable dental composition described herein. Dental composite (e.g. crowns) articles can be made from the curable composition described herein by casting the curable composition in contact with a mold and curing the composition. Alternatively, dental composites or articles (e.g. crowns) can be made by first curing the composition forming a mill blank and then mechanically milling the composition into the desired article.

Another method of treating a tooth surface comprises providing a dental composition as described herein wherein the composition is in the form of a (partially cured) curable, self-supporting, malleable structure having a first semi-finished shape; placing the curable dental composition on a tooth surface in the mouth of a subject; customizing the shape of the curable dental composition; and hardening the curable dental composition. The customization can occur in the patient's mouth or on a model outside the patient mouth such as described in U.S. Pat. No. 7,674,850 (Karim et al.); incorporated herein by reference.

EXAMPLES

All reactions were performed in round-bottomed flasks or glass jars or vials using unpurified commercial reagents.
Materials
Commercial reagents were used as received. Dichloromethane and toluene were obtained from EMD Chemicals Inc. (Gibbstown, N.J.). Glycidyl methacrylate, triphenylphosphine, cobalt(II) acetate tetrahydrate, pyridine, dimethylglyoxime, 1-methoxy-2-proponal, and dibutyltin dilaurate were obtained from Alfa Aesar (Ward Hill, Mass.). 2-2-biphenyl isocyanate was obtained from TCI America (Portland, Oreg.). Triphenyl antimony phenothiazine, methacrylic acid, and phenyl isocyanate were obtained from Sigma Aldrich (St. Louis, Mo.). Other materials included those listed in Table 1. Pentaerythritol triacrylate was obtained from Sartomer USA, LLC; Exton, Pa. Nalco 2329 k silica sol was obtained from Nalco Company; Naperville, Ill.

TABLE 1

| Acronym | Description and Source |
|---|---|
| 4-Meta | 4-Methacryloxyethyl trimellitic anhydride, Polysciences, Inc., Warrington, PA |
| BisGMA | (2,2-Bis[4-(2-hydroxy-3-methacryloyloxy-propoxy)phenyl]propane, Sigma Aldrich, St. Louis, MO |
| CPQ | Camphorquinone, Sigma Aldrich, St. Louis, MO |
| DPIHFP | Diphenyliodonium hexafluorophosphate (≥98%), Sigma Aldrich, St. Louis, MO |
| EDMAB | Ethyl 4-N,N-dimethylamino benzoate, Sigma Aldrich, St. Louis, MO |
| HEMA | Hydyroxyethyl methacrylate, Sigma Aldrich, St. Louis, MO |
| MHP | 6-methacryloyloxyhexyl phosphate - compound preparation described in U.S. Patent Publication No. 2009-0011388 (Craig, et al.) |
| UDMA | "ROHAMERE 6661-0" (diurethane dimethacrylate, CAS No. 41 137-60-4), Rohm Tech, Inc., Malden, MA |
| VAZO-67 | 2'-Azobis(2-methylbutyronitrile), CAS No. 13472-08-7, DuPont, Wilmington, DE |
| YbF$_3$ | Ytterbium(III) fluoride, Sigma Aldrich, St. Louis, MO |
| Z250 | filler prepared according to Example 1 of U.S. Pat. No. 4,503,169 |
| PROSTAB | Prostab 5198 - 4-hydroxy-TEMPO, Sigma Aldrich; St. Louis, MO USA |

Instrumentation

Nuclear magnetic resonance ("NMR") spectra (proton—$^1$H NMR and carbon—$^{13}$C NMR) were analyzed and recorded using an NMR spectrometer ("ULTRASHIELD PLUS 400 MHz NMR SPECTROMETER", Bruker Corporation, Billerica, Mass.). Attenuated Total Internal Reflectance-Fourier Transform Infrared ("ATR-FTIR") spectroscopy and analysis were performed on a "NEXUS 670 FT-IR E.S.P." instrument, Thermo Nicolet Corp., Madison, Wis.

Test Methods

Stress Test Method—Cusp Deflection

To measure stress development during the curing process, a slot was machined into a rectangular 15×8×8 mm aluminum block. The slot was 8 mm long, 2.5 mm deep, and 2 mm across, and was located 2 mm from an edge, thus forming a 2 mm wide aluminum cusp adjacent to a 2 mm wide cavity containing dental compositions being tested. A linear variable displacement transducer (MODEL GT 1000, used with an E309 ANALOG AMPLIFIER, both from RDP Electronics, United Kingdom) was positioned to measure the displacement of the cusp tip as the dental composition photocured at room temperature. Prior to testing, the slot in the aluminum block was sandblasted using ROCATEC PLUS SPECIAL SURFACE COATING BLASTING MATERIAL (3M ESPE, St. Paul, Minn.), treated with RELYX CERAMIC PRIMER (3M ESPE), and finally treated with a dental adhesive, ADPER EASY BOND (3M ESPE).

The slot was fully packed with a dental composition sample, which equaled approximately 100 mg of material. The dental composition sample was irradiated for 1 minute with a dental curing lamp (ELIPAR S-10, 3M ESPE) positioned almost in contact (<1 mm) with the material in the slot, then the displacement of the cusp in micrometers was recorded 9 minutes after the lamp was extinguished.

Depth of Cure Test Method

The depth of cure ("DOC") was measured for a test sample composition after curing. A test fixture with an open 8 millimeter stainless steel mold cavity was placed on a polyester film and filled with the sample composition. A second polyester film placed atop the resin and fixture was pressed to provide a level surface on the composition. The filled test fixture was placed on a white background surface and the composition was irradiated for 20 seconds using a dental curing light (3M DENTAL PRODUCTS CURING LIGHT 2500 or 3M ESPE ELIPAR FREELIGHT2, each made by 3M ESPE). After curing, the sample removed was from the mold and the uncured resin was gently removed by gently scraping materials from the bottom of the sample which was the side that was not irradiated with the curing light. The thickness of the remaining cured material was measured. The reported depths were the actual cured thickness in millimeters divided by 2.

Preparation of Glycidyl Methacrylate Dimer

An oven-dried, three-neck 250 mL round-bottomed flask was equipped with a magnetic stir bar, gas inlet adapter, and 50 mL pressure-equalizing addition funnel capped with a rubber septum, and a rubber septum. The apparatus was allowed to cool to room temperature under nitrogen. All ground-glass joints were coated with vacuum grease. Glycidyl methacrylate (25 mL, 26.95 g, 189.6 mmol) and VAZO-67 (0.0495 g, 0.257 mmol) were added to the reaction flask and the mixture was stirred. The addition funnel was charged with glycidyl methacrylate (50 mL, 53.90 g, 379.2 mmol) and VAZO-67 (0.0990 g, 0.515 mmol). The solutions of VAZO-67 in glycidyl methacrylate were sparged with nitrogen for 30 minutes after which the reaction was maintained under nitrogen. Next, cobalt(II) acetate tetrahydrate (0.0240 g, 0.0964 mmol), dimethylglyoxime (0.0360 g, 0.310 mmol), and pyridine (0.060 mL, 0.059 g, 0.74 mmol) were added to the pot. With stirring, the reaction was heated to 75° C. in an oil bath. The solution of glycidyl methacrylate and VAZO-67 was added to the pot dropwise over 1.5 hours. After an additional hour, another portion of VAZO-67 (0.0038 g, 0.0198 mmol) was added to the pot. The reaction was allowed to stir at 75° C. for an additional 18 hours. The reaction was then allowed to cool to room temperature. Residual glycidyl methacrylate monomer was removed under reduced pressure (approximately 0.16 mm Hg (21 Pa)) with gentle heating in an oil bath at 45° C. gently ramped to 95° C. The glycidyl methacrylate dimer product was then distilled from the reaction mixture using a short-path distillation apparatus. The glycidyl methacrylate dimer distilled at approximately 140° C. at a pressure of 0.15 mm Hg (20 Pa), and was obtained as a colorless to pale yellow, clear viscous liquid (17.60 g, 21.8%).

Preparation of Diacid 1

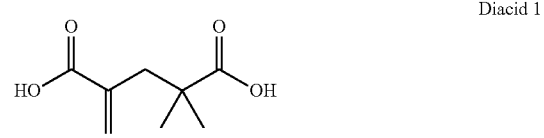

Diacid 1

"Diacid 1" was prepared as described in paragraph [0077] of U.S. Patent Publication No. 2012-0208965 (Joly et al., filed Jun. 27, 2011).

Preparation of AFO-1

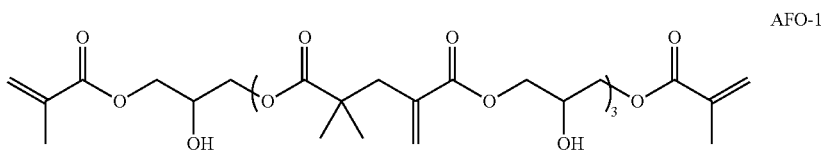

AFO-1

An 8 ounce (235 mL) jar equipped with a magnetic stir bar was charged with Diacid 1 (3.028 g, 17.5 mmol), glycidyl methacrylate dimer (10 g, 35 mmol), methacrylic acid (3.028 g, 35 mmol), toluene (39 g), triphenylphosphine (0.017 g, 0.06 mmol), triphenyl antimony (0.076, 0.2 mmol). The reaction was sealed with a plastic cap. With stirring, the mixture was heated to 100° C. in an oil bath. The reaction was sampled after 72 h and the $^1$H NMR spectrum was consistent with the desired product as a mixture of isomers. The reaction was cooled to room temperature and phenothiazine (2 mg, 150 ppm) was added. The solution was dried in vacuo with air bubbled through to provide AFO-1, a yellow, viscous material.

Preparation of AFO-2

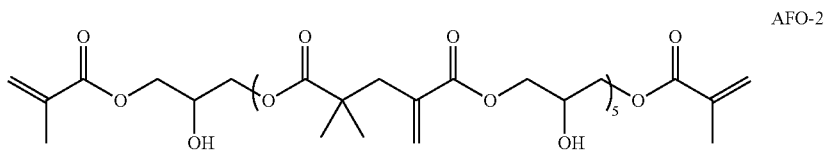

An 8 ounce (235 mL) jar equipped with a magnetic stir bar was charged with Diacid 1 (9.05 g, 52 mmol), glycidyl methacrylate dimer (22.4 g, 79 mmol), triphenylphosphine (0.09 g, 0.3 mmol), triphenyl antimony (0.76, 0.9 mmol), and toluene (93 g). The reaction was sealed with a plastic cap. With stirring, the mixture was heated to 100° C. in an oil bath. After 24 h, the reaction was sampled and the $^1$H NMR spectrum was consistent with the desired intermediate as a mixture of isomers. An excess of methacrylic acid (9.05 g, 79 mmol) was added to the reaction. With stirring, the mixture was heated to 100° C. in an oil bath. After an additional 36 h, the reaction was sampled and the $^1$H NMR spectrum was consistent with the desired product as a mixture of isomers. The reaction was cooled to room temperature and rinsed with saturated sodium bicarbonate to remove the excess methacrylic acid. The solution was then washed three times with water to remove any remaining salt. The solution was dried in vacuo with air bubbled through to provide AFO-2, a yellow, viscous material.

Preparation of AFO-3

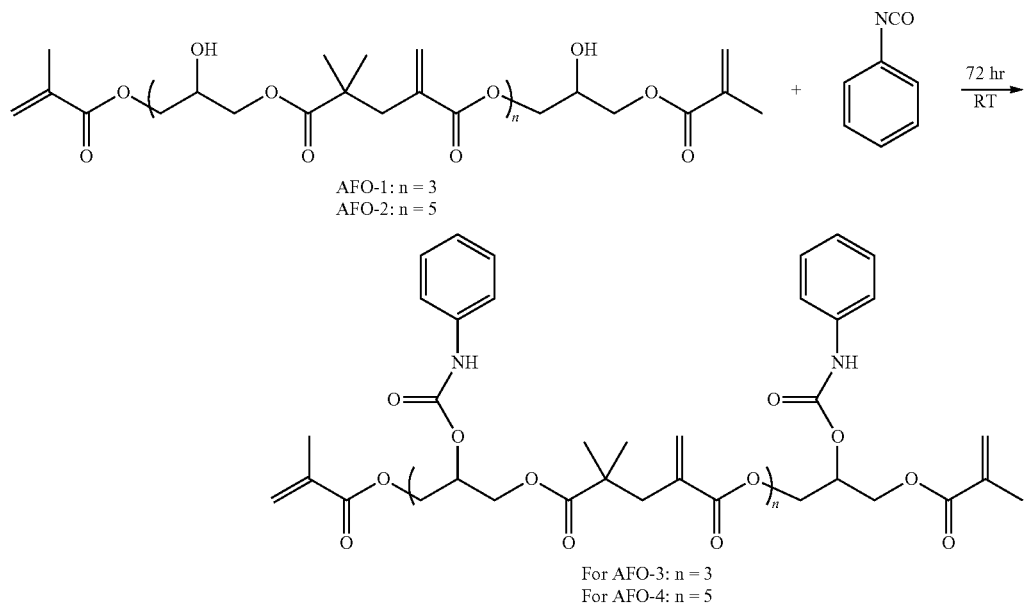

An 8 ounce (235 mL) jar equipped with a magnetic stir bar was charged with AFO-1 (4.2 g, 4.6 mmol), phenyl isocyanate (2.2 g, 18.6 mmol), dichloromethane (25 g), and 3 drops of dibutyltin dilaurate. The reaction was sealed with a plastic cap. With stirring, the mixture remained at room temperature. The reaction was sampled after 72 h and the $^1$H NMR spectrum and ATR-FTIR analysis were consistent with the desired product. Volatiles were removed under reduced pressure, as confirmed by $^1$H NMR spectroscopic analysis. The reaction yielded a viscous, yellow liquid.

Preparation of AFO-4

The same procedure was used as in the preparation of AFO-3, except that AFO-2 was used in place of AFO-1, and reactant amounts were adjusted to maintain stoichiometric amounts.

Preparation of AFO-5 and 3-methacryloxy propyl trimethoxysilane (6.36 g) in a 230 mL amber glass bottle. This mixture was then added to the silica sol with stirring over approximately 5 minutes.

TABLE 2

| | Nanoparticle compositions - grams | |
|---|---|---|
| Component | Ex 1 | Ex 2 |
| Silica sol - g | 100 | 100 |
| Methoxy propanol - g | 112.5 | 112.5 |
| 3-methacryloxy propyl trimethoxysilane - g | 6.36 | 6.36 |
| PROSTAB - 0.05 wt. % solution in water - g | 0.025 | 0.025 |
| Final wt. % solids | 50.2 | 39.5 |

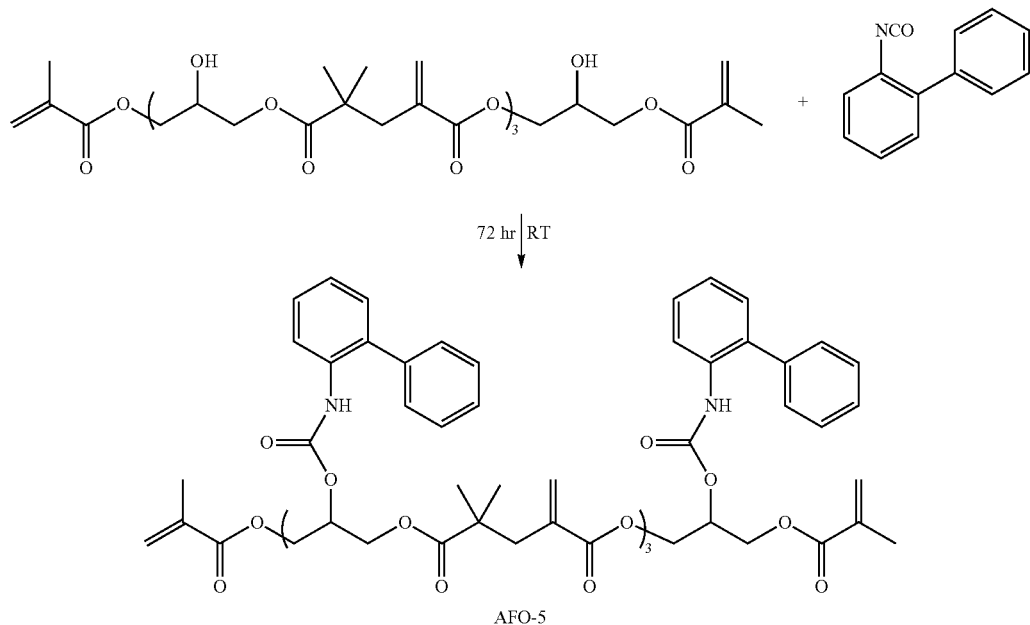

AFO-5

An 8 ounce (235 mL) jar equipped with a magnetic stir bar was charged with AFO-1 (4.6 g, 5.0 mmol), 2-biphenylisocyanate (3.9 g, 20.1 mmol), dichloromethane (40 g), and 3 drops of dibutyltin dilaurate. The reaction was sealed with a plastic cap. With stirring, the mixture remained at room temperature. The reaction was sampled after 72 h and the $^1$H NMR spectrum and ATR-FTIR analysis were consistent with the desired product. Volatiles were removed under reduced pressure, as confirmed by $^1$H NMR spectroscopic analysis. The reaction yielded a viscous, yellow liquid.

Examples 1 and 2: Nanoparticle Fillers Functionalized with 3-methacryloxy propyl trimethoxysilane Compositions were prepared having the components shown in Table 2 according to the following procedure:

100 g of silica sol (NALCO 2329K sol; 41.33 wt. %) was added to a 16 ounce (470 mL) glass bottle with PTFE-wrapped threads and stirred with a magnetic stir bar. A solution was prepared by mixing methoxy propanol (112.5 g), PROSTAB (0.0250 g of a 0.05 wt. % solution in water), The 16 ounce (470 mL) glass jar was then sealed with a PTFE-lined metal cap, PTFE tape, and electrical tape. The reaction was heated to 90° C. with stirring. After approximately 18 hours, the reaction mixture was transferred to a 500 mL round-bottomed flask and concentrated under reduced pressure to approximately 45 wt % solids (approximately half the original volume). Approximately 110 grams of methoxy propanol was added to lower the solids back to approximately 20 wt %. The solution was then concentrated under reduced pressure again to provide an example of a "filler solution" having approximately 45 wt % functionalized nanoparticle solids (about 100 mL).

The wt % solids of each example was determined by adding approximately 0.250 g of the final solution to an aluminum pan and drying in an oven set at 125° C. for 45 minutes. The sample was then removed from the oven, allowed to cool to room temperature, and the mass of the dried sample was measured and used to calculate percent solids in the nanoparticle solution.

Examples 3 to 6, and Control Example C1—Hard Coats

Hard coat solutions for each of Examples 3 to 6 ("Ex 3" to "Ex 6") and Control Example 1 ("C1") were prepared by combining the methoxy propanol solution of functionalized silica nanoparticles from Table 1 (Ex 1), pentaerythritol triacrylate, IRGACURE 651, and AFO-3 in the amounts shown in Table 3 in a 20 mL glass vial. 1-Methoxy-2-propanol was added to bring the weight percent solids of the solution to 50 percent. Each solution was mixed well and then sonicated for 2-5 minutes.

TABLE 3

| | Hard coat formulations - grams | | | | |
|---|---|---|---|---|---|
| Component | Ex 3 | Ex 4 | Ex 5 | Ex 6 | C1 |
| AFO-3 | 0.05 | 0.125 | 0.25 | 0.375 | 0 |
| Filler solution of Ex 1 | 4.98 | 4.98 | 4.98 | 4.98 | 4.98 |
| Pentaerythritol triacrylate | 2.40 | 2.32 | 2.20 | 2.08 | 2.45 |
| IRGACURE 651 | 0.05 | 0.05 | 0.05 | 0.05 | 0.05 |
| Additional 1-Methoxy-2-propanol | 2.52 | 2.52 | 2.52 | 2.52 | 2.52 |
| wt. % AFO-3 | 1 | 2.5 | 5.0 | 7.5 | 0 |

The solutions were each coated onto 6 inch by 14 inch (15 cm by 36 cm) sheets of 5 mil (127 micrometers) thick polyethylene terephthalate ("PET") film (prepared according to Example 29 of U.S. Pat. No. 6,893,731 B2) using a #10 wire-wound rod (obtained from RD Specialties, Webster, N.Y.). The coated samples were dried in an oven set at 75° C. for 30 minutes. The coatings were then cured by irradiating with UV light (1000 mJ/cm$^2$, UVB) using a UV processor (Fusion UV System, Inc., Gaithersburg, Md.) equipped with an H-bulb and operated under nitrogen atmosphere at a line speed of 24 feet/min (7.3 meters/min), for 2 passes, to provide hard coats.

After irradiation, the hard coats were measured for film curl, hard coat thickness, and pencil hardness. Results were as shown in Table 4. The film curl was determined on a 7.6 by 7.6 cm square sample was cut from the center of the hard coat. The hard coat was still on the PET substrate. The sample was placed on a flat surface, and the height of each corner was measured using a ruler. The total curl was determined by summing the height of the four corners.

The film thickness was measured at each corner of the 7.6 by 7.6 cm square and in the middle of each side (eight measurements total) and average film thickness was calculated using these eight measurements. The film thickness was measured using a MITUTOYO DIGITAL DIAL GAUGE, MODEL ID-F125E (Mitutoyo Corp., Aurora, Ill.).

The pencil hardness was measured on each hard coat using an ELCOMETER 3086 MOTORIZED PENCIL HARDNESS TESTER (obtained from Elcometer Inc. of Rochester Hills, Mich.) with a 7.5 N load, following ASTM D3363.

TABLE 4

| | Hard Coat Properties Example | | | | |
|---|---|---|---|---|---|
| | C1 | Ex 3 | Ex 4 | Ex 5 | Ex 6 |
| | Film Curl Measurements | | | | |
| Corner height measurements (mm) | 13.0 | 9.0 | 8.5 | 6.0 | 7.0 |
| | 3.0 | 3.0 | 3.0 | 4.0 | 2.0 |
| | 10.5 | 8.5 | 8.0 | 5.0 | 6.5 |
| | 2.0 | 3.0 | 3.0 | 3.0 | 2.0 |
| Total corner height (mm) | 28.5 | 23.5 | 22.5 | 18.0 | 17.5 |
| Relative to Control (%) | 100 | 82.5 | 79.0 | 63.2 | 61.4 |

TABLE 4-continued

| | Hard Coat Properties Example | | | | |
|---|---|---|---|---|---|
| | C1 | Ex 3 | Ex 4 | Ex 5 | Ex 6 |
| | Hard Coat Thickness | | | | |
| Corner & side measurements (micrometers) | 7.0 | 7.0 | 7.0 | 6.0 | 5.0 |
| | 7.0 | 7.0 | 7.0 | 5.0 | 6.0 |
| | 9.0 | 7.0 | 7.0 | 5.0 | 6.0 |
| | 7.0 | 7.0 | 7.0 | 6.0 | 6.0 |
| | 7.0 | 7.0 | 7.0 | 6.0 | 7.0 |
| | 6.0 | 7.0 | 7.0 | 6.0 | 6.0 |
| | 9.0 | 7.0 | 7.0 | 6.0 | 6.0 |
| | 8.0 | 7.0 | 7.0 | 6.0 | 5.0 |
| Avg Hard coat Thickness (micrometers) | 7.5 | 7.0 | 7.0 | 5.8 | 5.9 |
| Standard Deviation | 1.1 | 0.0 | 0.0 | 0.5 | 0.6 |
| Relative to Control (%) | 100 | 93.3 | 93.3 | 76.7 | 78.3 |
| | Hardness | | | | |
| Pencil hardness | 3H | 3H | 3H | 2H | 3H |

Preparation of C2-C5 and Ex 7-Ex 9: The appropriate masses of methacrylate-based monomers (e.g. MHP, UDMA, HEMA, BisGMA, and AFO or AFM) were added to a mixing cup and mixed to provide a homogeneous mixture. Initiator components (e.g. DPIPF6, CPQ, and EDMAB) were then added, and the resultant mixture was mixed until all solids had completely dissolved. Fillers were then added (e.g. YbF3 and Filler) and the resultant mixture was again mixed to provide a homogeneous paste. The paste was allowed to sit for 24 hours at room temperature, and mixed again prior to use to ensure homogeneity.

TABLE 5

| | Formulations for Control Examples C2 to C5 and Examples Ex 7 to Ex 9 | | | | | | |
|---|---|---|---|---|---|---|---|
| | C2 | C3 | C4 | C5 | Ex 7 | Ex 8 | Ex 9 |
| DPIPF6 (g) | 0.36 | 0.36 | 0.36 | 0.36 | 0.36 | 0.36 | 0.36 |
| CPQ (g) | 0.28 | 0.28 | 0.28 | 0.28 | 0.28 | 0.28 | 0.28 |
| EDMAB (g) | 0.8 | 0.8 | 0.8 | 0.8 | 0.8 | 0.8 | 0.8 |
| MHP (g) | 18.5 | 18 | 17.84 | 17.68 | 17.68 | 17.16 | 16.88 |
| UDMA (g) | 2.46 | 2.38 | 2.38 | 2.38 | 2.38 | 2.32 | 2.3 |
| HEMA (g) | 22 | 21.38 | 20.94 | 20.5 | 20.5 | 19.9 | 19.6 |
| BisGMA (g) | 29.6 | 28.8 | 28.4 | 28 | 28 | 27.18 | 26.78 |
| AFO-5 (g) | 0 | 0 | 0 | 0 | 4 | 6 | 7 |
| AFM-1 (g) | 0 | 2 | 3 | 4 | 0 | 0 | 0 |
| YbF$_3$ (g) | 1 | 1 | 1 | 1 | 1 | 1 | 1 |
| Z250 Filler (g) | 11.6 | 11.6 | 11.6 | 11.6 | 11.6 | 11.6 | 11.6 |

The Control Examples and Examples having the formulations according to Table 5 were tested according to the Stress Test Method and the Depth of Cure Test Method, with results as summarized in Table 6.

TABLE 6

| | Stress Test and Depth of Cure Results | |
|---|---|---|
| | Stress Test - Cusp Deflection, micrometers | Depth of Cure, mm |
| C2 | 6.59 | 3.46 |
| C3 | 4.51 | 3.01 |
| C4 | 3.47 | 2.78 |
| C5 | 2.83 | 2.69 |
| Ex 7 | 4.2 | 3.36 |
| Ex 8 | 3.64 | 3.28 |
| Ex 9 | 3.32 | 3.22 |

This disclosure provides the following illustrative embodiments:

1. An addition-fragmentation oligomer of the formula

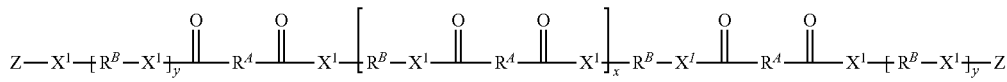

wherein
$R^A$ is

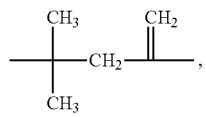

$R^B$ a (hetero)hydrocarbyl group, wherein at least one $R^B$ is substituted with a high refractive index group,
$X^1$ is —O— or $NR^5$—, where $R^5$ is H or $C_1$-$C_4$ alkyl;
Z comprises an ethylenically unsaturated polymerizable group;
y is 0 or 1;
x is 0 or 1.

2. The addition-fragmentation oligomer of embodiment 1, wherein at least 50% of the $R^B$ units are substituted by a high refractive index group.

3. The addition-fragmentation oligomer of embodiment 1, wherein at least 75% of the $R^B$ units are substituted by a high refractive index group.

4. The addition-fragmentation oligomer of any of embodiments 1-3, wherein the high refractive index group is selected from benzyl, 2-, 3-, and 4-biphenyl, 1-, 2, 3-, 4-, and 9-fluorenyl, 4-(1-methyl-1-phenethyl)phenoxyethyl; phenylthio; 1-, 2-, 3- and 4-napthyl, 1- and 2-naphthylthio; 2,4,6-tribromophenoxy; 2,4-dibromophenoxy; 2-bromophenoxy; 1-, and 2-naphthyloxy; 3-phenoxy-; 2-, 3- and 4-phenylphenoxy; 2,4-dibromo-6-sec-butylphenyl; 2,4-dibromo-6-isopropylphenyl; 2,4-dibromophenyl; pentabromobenzyl and pentabromophenyl.

5. The addition-fragmentation oligomer of any of the previous embodiments wherein Z comprises a (meth)acrylate or vinyl group.

6. The addition-fragmentation oligomer of any of the previous embodiments derived from A compounds of the formula:
$R^1$—O—CO—$R^A$—CO—O—$R^1$, wherein $R^A$ is a 1-methylene-3,3-dimethylpropyl group and $R^1$ is H, alkyl, aryl or $R^{FG}$, where $R^{FG}$ is an aryl or an alkyl further substituted with a nucleophilic or electrophilic functional group.

7. The addition-fragmentation oligomer of embodiment 6 derived from B compounds of the formula:
$X^2$—$R^B$—$X^2$, wherein $R^B$ is a (hetero)hydrocarbyl group and $X^2$ is functional group reactive with the functional groups of the A compound.

8. The addition-fragmentation oligomer of embodiment 7 wherein the compound of the formula $X^2$—$R^B$—$X^2$ is selected from difunctional epoxides, diols, aziridines, isocyanates and diamines.

9. The addition fragmentation of embodiment 7 where reaction between the A compounds and B compounds yields an intermediate oligomer of the formula:

A and B compounds may have the structure

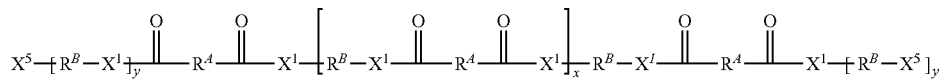

wherein
$R^A$ is

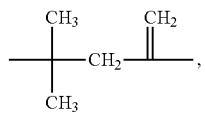

$R^B$ a (hetero)hydrocarbyl group, wherein at least one $R^B$ contains a high refractive index group,
$X^1$ is —O— or $NR^5$—, where $R^5$ is H or $C_1$-$C_4$ alkyl;
Z comprises an ethylenically unsaturated polymerizable group;
$X^5$ is a terminal functional group selected from —$OR^1$ of the A compounds or $X^2$ of the B compounds;
y is 0 or 1;
x is 0 or 1.

10. The addition-fragmentation oligomer of any of the previous embodiments where y is 1.

11. The addition-fragmentation oligomer of any of embodiments 1-9 where y is 0.

12. The addition-fragmentation oligomer of any of embodiments 1-11 where x+y is 0 to 60.

13. The addition-fragmentation oligomer of any of embodiments 1-11 where x+y is 1 to 20.

14. The addition-fragmentation oligomer of any of the previous embodiments where the Z group is derived from an ethylenically unsaturated compound of the formula:
$(Z)_d$—$X^3$, where Z comprises an ethylenically unsaturated group, and $X^3$ is a functional group reactive with the terminal functional groups of the intermediate oligomer.

15. The addition-fragmentation oligomer of embodiment 14 wherein the compound of the formula $(Z)_d$—$X^3$ is of the formula:
$Y^1$—$R^3$—O—CO—$CR^2$=$CH_2$, where $Y^1$ is an electrophilic functional group reactive with terminal electrophilic functional groups of the intermediate oligomer, $R^3$ is an alkylene, $R^2$ is H or $CH_3$.

16. The addition-fragmentation oligomer of embodiment 14 wherein the compound of the formula $(Z)_d—X^3$ is of the formula:

$Y^2—R^3—O—CO—CR^2=CH_2$, where $Y^2$ is an nucleophilic functional group reactive with the electrophilic functional groups of the intermediate oligomer, $R^3$ is an alkylene, $R^2$ is H or $CH_3$.

17. The addition-fragmentation oligomer of any of the previous embodiments wherein the high refractive index group is derived from a compound of the formula: $(R^{RI})_d—X^5$, where $R^{RI}$ comprises high refractive index group, $X^5$ is a reactive functional group, and subscript d is at least 1.

18. A polymerizable composition comprising the addition-fragmentation oligomer of any of embodiments 1-17, at least one free-radically polymerizable monomer, and an initiator.

19. The polymerizable composition of embodiment 18 comprising:
   a) 85 to 100 parts by weight of an (meth)acrylic acid ester;
   b) 0 to 15 parts by weight of an acid functional ethylenically unsaturated monomer;
   c) 0 to 10 parts by weight of a non-acid functional, ethylenically unsaturated polar monomer;
   d) 0 to 5 parts vinyl monomer; and
   e) 0 to 100 parts of a multifunctional (meth)acrylate; based on 100 parts by weight total monomer a) to d), and
   f) 0.1 to 12 parts by weight of the addition-fragmentation oligomer, based on 100 parts by weight of a) to e), and
   g) an initiator.

20. The polymerizable composition of embodiment 19 further comprising 0.01 to 100 parts of a multifunctional (meth)acrylate.

21. The polymerizable composition of embodiments 18 to 20 comprising a photoinitiator.

22. The polymerizable composition of any of embodiments 18 to 20 wherein the initiator is a thermal initiator.

23. The polymerizable composition of any of embodiments 18 to 22 containing less than 0.01 wt. % cobalt compounds.

24. The polymerizable composition of any of embodiments 18-23 further comprising an inorganic filler.

25. The polymerizable composition of embodiment 24 wherein the filler is a surface-modified silica filler.

26. An article comprising a layer of the polymerizable composition of any of embodiments 18-25 on a substrate.

27. An article comprising the cured polymerizable composition of any of embodiments 18-25 on a substrate.

28. A method of bonding two substrates together comprising the steps of coating the polymerizable composition of any of embodiments 18-25 to a surface of one or both substrates, contacting the coated surfaces, optionally with pressure, and curing the polymerizable compositions.

29. A method of bonding two substrates together comprising the steps of coating the polymerizable composition of any of embodiments 18-25 to a surface of one or both substrates, wherein he coating of polymerizable composition is at least partially cured, contacting the coated surfaces optionally with pressure, and further curing the polymerizable compositions if necessary.

30. A hardcoat composition comprising one or more multifunctional (meth)acrylate monomers or (meth)acrylate oligomers, and the addition-fragmentation oligomer of any of embodiments 1 to 17.

31. The hardcoat composition of embodiment 30 comprising:
   a) 0.1-10 wt. % of the addition fragmentation oligomer;
   b) 20-80 wt. % of multifunctional (meth)acrylate monomers and/or multifunctional (meth)acrylate oligomers,
   c) 0 to 25 wt. % range of (meth)acrylate diluent, (0-25 wt. %); and
   d) 20 to 75 wt. % of silica.

32. A curable dental composition comprising:
   a) at least one dental resin comprising at least two ethylenically unsaturated group;
   b) an addition-fragmentation oligomer of any embodiments 1 to 17; and
   c) optionally an inorganic oxide filler.

33. The dental composition of embodiment 32 wherein the ethylenically unsaturated groups of the dental resin are (meth)acrylate groups.

34. The dental composition of any of the preceding embodiments 32-33 wherein the dental resin comprises an aromatic monomer having a refractive index of at least 1.50.

35. The dental composition of any of the preceding embodiments 32-33 wherein the dental resin is a low volume shrinkage resin.

36. The dental composition of any of the preceding embodiments 32-35 wherein the dental resin is an isocyanurate resin, a tricyclodecane resin, cyclic allylic sulfide resins; methylene dithiepane silane resins; and poly(meth)acryloyl-containing resins, or mixtures thereof.

37. The dental composition of any of the preceding embodiments 32-36 wherein the hardened dental composition exhibits a stress deflection no greater than 4.0.

38. The dental composition of any of the preceding embodiments 32-37 wherein the dental composition further comprises at least one other (meth)acrylate monomer is selected from ethoxylated bisphenol A dimethacrylate, 2-hydroxyethyl methacrylate, bisphenol A diglycidyl dimethacrylate, urethane dimethacrylate, triethlyene glycol dimethacrylate, glycerol dimethacrylate, ethylenegylcol dimethacrylate, neopentylglycol dimethacrylate (NPGDMA), polyethyleneglycol dimethacrylate, and mixtures thereof.

39. The dental composition of any of the preceding embodiments 32-38 wherein the inorganic oxide filler comprises nanoparticles.

40. The dental composition of embodiment 39 wherein the inorganic oxide nanoparticles comprise silica, zirconia, or mixtures thereof.

41. The dental composition of embodiments 39 or 40 wherein the inorganic oxide nanoparticles are in the form of nanoclusters.

42. The dental composition of any of the preceding embodiments 32-41 comprising a surface modified inorganic oxide filler.

43. A method of treating a tooth surface, the method comprising
   a) providing a curable dental resin of any of embodiments 32-42;
   b) placing the dental composition on a tooth surface in the mouth of a subject; and
   c) hardening the hardenable dental composition.

44. The method of embodiment 43 wherein the dental composition is a dental restoration composition.

45. A dental article comprising the curable dental composition of embodiments 32-42 at least partially cured.

46. A method of treating a tooth surface, the method comprising
   providing an at least partially hardened dental article according to claim 45, adhering the dental article on a tooth surface in the mouth of a subject.

47. A universal dental restorative comprising:
   a) 15-30 wt. % of a curable dental resin comprising at least two polymerizable, ethylenically unsaturated groups;

b) 70-85 wt. % of an inorganic filler, preferably a surface modified filler;
c) 0.1 to 10 parts by weight of the addition-fragmentation oligomer of any of claim 1-17, relative to 100 parts by weight of a) and b),
said curable composition further comprising an initiator and; <2%, stabilizers, pigments, etc.

48. A flowable restorative composite comprising:
a) 25-50 wt. % of a curable dental resin comprising at least two polymerizable, ethylenically unsaturated groups;
b) 30-75 wt. % of an inorganic filler;
c) 0.1 to 10 parts by weight of the addition-fragmentation oligomer of any of embodiments 1-17, relative to 100 parts by weight of a) and b).
d) an initiator;
e) <2% stabilizers and pigments, and
f) optionally 5-60 wt. % monomers having an acid-functional group.

49. A resin-modified glass-ionomer adhesive comprising:
a) 10-25 wt. % of a partially (meth)acrylated poly(meth)acrylic acid;
b) 5-20% of a hydroxyalkyl (meth)acrylate;
c) 30-60% of fluoroaluminosilicate (FAS) acid reactive glass);
d) 0-20% non-acid reactive fillers, preferably surface-treated;
e) 10-20% water; and
f) 0.1 to 10 wt. % of the addition-fragmentation oligomer of any of embodiments 1-17, relative to 100 parts by weight of a) and b)
g) an initiator.

50. The resin-modified glass ionomer adhesive of embodiment 49 wherein the fluoroaluminosilicate is a silane methacrylate surface-treated floroaluminosilicate.

51. A dental adhesive comprising:
a) 30-80 wt. % mono (meth)acrylate) monomers;
b) 1-10 wt. % polyfunctional (meth)acrylate monomers;
c) 5-60 wt. % monomers having a acid-functional group (including phosphate, phosphonate, carboxylate, sulfonic acids)
d) 0-10, preferably 1-10 wt. % poly(meth)acrylic acid methacrylate monomers;
e) 0.1 to 10 wt. % of the addition-fragmentation oligomer of any of embodiments 1-17, relative to 100 parts by weight of a) to d);
f) an initiator,
g) 0-30% inorganic filler, preferably surface modified, relative to 100 parts by weight of a) to d);
h) 0 to 25 wt. % solvent relative to 100 parts by weight of a) to d);
i) 0 to 25 wt. % water relative to 100 parts by weight of a) to d); and <2% stabilizers and pigments.

The invention claimed is:
1. An addition-fragmentation oligomer of the formula

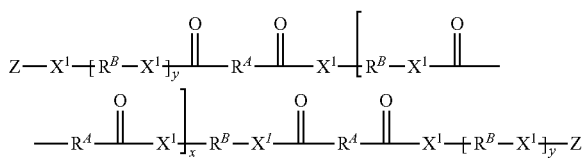

wherein
$R^A$ is

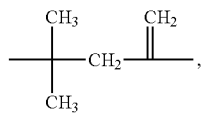

$R^B$ a (hetero)hydrocarbyl group, wherein at least 50% of the $R^B$ units are substituted with a high refractive index group,
$X^1$ is —O— or $NR^5$—, where $R^5$ is H or $C_1$-$C_4$ alkyl;
Z comprises an ethylenically unsaturated polymerizable group;
y is 0 or 1;
x is 0 or 1.

2. The addition-fragmentation oligomer of claim 1, wherein at least 75% of the $R^B$ units are substituted by a high refractive index group.

3. The addition-fragmentation oligomer of claim 1, wherein the high refractive index group is selected from benzyl, 2-, 3-, and 4-biphenyl, 1-, 2, 3-, 4-, and 9-fluorenyl, 4-(1-methyl-1-phenethyl)phenoxyethyl; phenylthio; 1-, 2-, 3- and 4-napthyl, 1- and 2-naphthylthio; 2,4,6-tribromophenoxy; 2,4-dibromophenoxy; 2-bromophenoxy; 1-, and 2-naphthyloxy; 3-phenoxy-; 2-, 3- and 4-phenylphenoxy; 2,4-dibromo-6-sec-butylphenyl; 2,4-dibromo-6-isopropylphenyl; 2,4-dibromophenyl; pentabromobenzyl and pentabromophenyl.

4. The addition-fragmentation oligomer of claim 1 derived from A compounds of the formula:
$R^1$—O—CO—$R^A$—CO—O—$R^1$, wherein $R^A$ is a 1-methylene-3,3-dimethylpropyl group and $R^1$ is H, alkyl, aryl or $R^{FG}$, where $R^{FG}$ is an aryl or an alkyl further substituted with a nucleophilic or electrophilic functional group.

5. The addition-fragmentation oligomer of claim 4 derived from B compounds of the formula:
$X^2$—$R^B$—$X^2$, wherein $R^B$ is a (hetero)hydrocarbyl group and $X^2$ is functional group reactive with the functional groups of the A compound.

6. The addition-fragmentation oligomer of claim 5 wherein the compound of the formula $X^2$—$R^B$—$X^2$ is selected from difunctional epoxides, diols, aziridines, isocyanates and diamines.

7. The addition-fragmentation oligomer of claim 1 where x+y is 0 to 2.

8. The addition-fragmentation oligomer of claim 1 where x+y is 1 to 2.

9. A polymerizable composition comprising the addition-fragmentation oligomer of claim 1, at least one free-radically polymerizable monomer, and an initiator.

10. The polymerizable composition of claim 9 comprising:
a) 85 to 100 parts by weight of an (meth)acrylic acid ester;
b) 0 to 15 parts by weight of an acid functional ethylenically unsaturated monomer;
c) 0 to 10 parts by weight of a non-acid functional, ethylenically unsaturated polar monomer;
d) 0 to 5 parts vinyl monomer; and
e) 0 to 100 parts of a multifunctional (meth)acrylate; based on 100 parts by weight total monomer a) to d), and f) 0.1 to 12 parts by weight of the addition-fragmentation oligomer, based on 100 parts by weight of a) to e), and
g) an initiator.

11. The polymerizable composition of claim 10 further comprising 0.01 to 100 parts of a multifunctional (meth)acrylate based on 100 parts by weight total monomer a) to d).

12. The polymerizable composition of claim 9 further comprising an inorganic filler.

13. An article comprising the cured polymerizable composition of claim 9 on a substrate.

14. A method of bonding two substrates together comprising the steps of coating the polymerizable composition of claim 9 to a surface of one or both substrates, contacting the coated surfaces, optionally with pressure, and curing the polymerizable compositions.

15. A hardcoat composition comprising one or more multifunctional (meth)acrylate monomers or (meth)acrylate oligomers, and the addition-fragmentation oligomer of claim 1.

16. The hardcoat composition of claim 15 comprising:
a) 0.1-10 wt. % of the addition fragmentation oligomer;
b) 20-80 wt. % of multifunctional (meth)acrylate monomers and/or multifunctional (meth)acrylate oligomers,
c) 0 to 25 wt. % range of (meth)acrylate diluent, (0-25 wt. %); and
d) 20 to 75 wt. % of silica.

17. A curable dental composition comprising:
a) at least one dental resin comprising at least two ethylenically unsaturated group;
b) an addition-fragmentation oligomer of claim 1; and
c) optionally an inorganic oxide filler.

18. The dental composition of claim 17 wherein the inorganic oxide filler comprises nanoparticles.

* * * * *

UNITED STATES PATENT AND TRADEMARK OFFICE
CERTIFICATE OF CORRECTION

PATENT NO. : 9,730,864 B2
APPLICATION NO. : 15/112220
DATED : August 15, 2017
INVENTOR(S) : Ann Fornof It is certified that error appears in the above-identified patent and that said Letters Patent is hereby corrected as shown below:

In the Specification

Column 1,
Line 66, delete "(B-A)X" and insert -- $(B-A)_X$ --, therefor.

Column 5,
Line 4, after "relief" insert -- . --.

Column 10,
Line 4, delete "RB" and insert -- $R^B$ --, therefor.

Column 15,
Lines 26 & 27, delete "based on 100 parts by weight total monomer." and insert the same on Column 15, Line 27, as a new paragraph.

Column 51,
Line 7, delete "<2%, stabilizers, pigments, etc." and insert the same on Column 51, Line 8, as a new paragraph.

Signed and Sealed this
Third Day of October, 2017

Joseph Matal
*Performing the Functions and Duties of the*
*Under Secretary of Commerce for Intellectual Property and*
*Director of the United States Patent and Trademark Office*